(12) United States Patent
Mah et al.

(10) Patent No.: US 7,830,519 B2
(45) Date of Patent: Nov. 9, 2010

(54) METHOD AND DEVICE FOR ANALYTE MEASUREMENT

(75) Inventors: Christopher D. Mah, Skokie, IL (US); Joel Orlinsky, Ingleside, IL (US); Dilip Mehta, Mount Prospect, IL (US); Dean Milani, Antioch, IL (US)

(73) Assignee: Vivum Nexus LLC, Chapel Hill, NC (US)

( * ) Notice: Subject to any disclaimer, the term of this patent is extended or adjusted under 35 U.S.C. 154(b) by 819 days.

(21) Appl. No.: 11/677,657

(22) Filed: Feb. 22, 2007

(65) Prior Publication Data

US 2007/0197885 A1    Aug. 23, 2007

Related U.S. Application Data

(60) Provisional application No. 60/775,820, filed on Feb. 22, 2006.

(51) Int. Cl.
*G01N 21/00* (2006.01)
(52) U.S. Cl. .................................... 356/434
(58) Field of Classification Search ............ None
See application file for complete search history.

(56) References Cited

U.S. PATENT DOCUMENTS

| | | | |
|---|---|---|---|
| 4,714,341 A | 12/1987 | Hamaguri et al. | |
| 4,975,581 A | 12/1990 | Robinson et al. | |
| 5,077,476 A | 12/1991 | Rosenthal | |
| 5,099,123 A | 3/1992 | Harjunmaa | |
| 5,112,124 A | 5/1992 | Harjunmaa et al. | |
| 5,137,023 A * | 8/1992 | Mendelson et al. | 600/316 |
| 5,183,042 A | 2/1993 | Harjunmaa et al. | |
| 5,254,848 A | 10/1993 | Kashimura | |
| 5,254,858 A | 10/1993 | Wolfman et al. | |
| 5,257,086 A | 10/1993 | Fateley et al. | |
| 5,291,884 A | 3/1994 | Heinemann et al. | |
| 5,435,309 A | 7/1995 | Thomas et al. | |
| 5,477,853 A | 12/1995 | Farkas et al. | |
| 5,533,509 A * | 7/1996 | Koashi et al. | 356/41 |
| 5,551,422 A | 9/1996 | Simonsen et al. | |
| 5,638,816 A | 6/1997 | Kiani-Azarbayjany et al. | |
| 5,657,754 A | 8/1997 | Rosencwaig | |

(Continued)

OTHER PUBLICATIONS

Lorber et al., Net Analyte Signal Calculation in Multivariate Calibration, Apr. 15, 1997, Analytical Chemistry vol. 69, No. 8, pp. 1620-1626.*

(Continued)

*Primary Examiner*—Gregory J Toatley, Jr.
*Assistant Examiner*—Juan D Valentin
(74) *Attorney, Agent, or Firm*—Reed Smith, LLP

(57) ABSTRACT

A device for non-invasively measuring concentration of one or more analytes in a living subject or a biological sample, wherein the device includes several light sources, a system for controlling the timing and intensity of the light source outputs, a system for passing the light through the subject or sample, a system for measuring the amount of light transmitted, and a system for relating the measurement to the concentration of the analyte in question. The light sources are narrow band sources at different wavelengths, and are capable of being rapidly switched between two levels of intensity. The actual number of light sources required and the wavelengths of the sources are dependent upon the specific analyte being measured.

38 Claims, 15 Drawing Sheets

U.S. PATENT DOCUMENTS

| | | | |
|---|---|---|---|
| 5,743,262 | A | 4/1998 | Lepper, Jr. et al. |
| 5,782,755 | A | 7/1998 | Chance |
| 5,949,540 | A * | 9/1999 | Matsuoka et al. ............ 356/326 |
| 5,957,841 | A | 9/1999 | Maruo et al. |
| 6,226,089 | B1 * | 5/2001 | Hakamata .................... 356/432 |
| 6,263,222 | B1 | 7/2001 | Diab et al. |
| 6,266,546 | B1 | 7/2001 | Steuer et al. |
| 6,391,647 | B1 | 5/2002 | Sperling et al. |
| 6,400,971 | B1 | 6/2002 | Finarov et al. |
| 6,442,411 | B1 | 8/2002 | Guthermann |
| 6,466,807 | B1 | 10/2002 | Dobson et al. |
| 6,526,298 | B1 | 2/2003 | Khalil et al. |
| 6,542,762 | B1 | 4/2003 | Alam et al. |
| 6,552,221 | B1 | 4/2003 | Hallinan et al. |
| 6,608,678 | B1 | 8/2003 | Potyrailo et al. |
| 6,615,061 | B1 | 9/2003 | Khalil et al. |
| 6,625,480 | B2 | 9/2003 | Hwang et al. |
| 6,636,752 | B1 | 10/2003 | Madarasz et al. |
| 6,650,915 | B2 | 11/2003 | Routt et al. |
| 6,741,875 | B1 | 5/2004 | Pawluczyk et al. |
| 6,816,241 | B2 | 11/2004 | Grubisic |
| 6,859,275 | B2 | 2/2005 | Fateley et al. |
| 6,865,408 | B1 | 3/2005 | Abbink et al. |
| 6,889,075 | B2 | 5/2005 | Marchitto et al. |
| 6,901,285 | B2 | 5/2005 | Schreck |
| 6,912,084 | B2 | 6/2005 | Freund |
| 6,931,268 | B1 | 8/2005 | Kiani-Azarbayjany et al. |
| 6,957,094 | B2 | 10/2005 | Chance et al. |
| 6,968,221 | B2 | 11/2005 | Rosenthal |
| 7,027,849 | B2 | 4/2006 | Al-Ali |
| 7,098,037 | B2 | 8/2006 | Haas et al. |
| 7,167,299 | B1 | 1/2007 | Raghavan et al. |
| 7,167,734 | B2 | 1/2007 | Khalil et al. |
| 7,196,789 | B2 | 3/2007 | Senturia |
| 2002/0137993 | A1 | 9/2002 | Pickard |
| 2003/0048432 | A1 | 3/2003 | Jeng et al. |
| 2004/0073101 | A1 | 4/2004 | Chance |
| 2004/0111016 | A1 | 6/2004 | Casscells et al. |
| 2004/0176670 | A1 | 9/2004 | Takamura et al. |
| 2006/0017923 | A1 | 1/2006 | Ruchti et al. |

OTHER PUBLICATIONS

Mark A. Arnold and Gary W. Small, Analytical Chemistry, vol. 77, No. 17, Sep. 1, 2005, pp. 5429-5439 entitled: Noninvasive Glucose Sensing.

Stephen E. Bialkowski, Analytical Chemistry, 1986 58: pp. 2563-2567.

John A. Decker, Jr., Spectrometric Techniques, vol. 1, Academic Press 1977, Chapter 5 pp. 189-227, entitled Hadamard-Transform Spectroscopy.

R.A. Deverse, R.M. Hammaker, and W.G. Fateley, Applied Spectroscopy, vol. 54, No. 12, 2000, pp. 1751-1758, entitled: Realization of the Hadamard Multiplex Advantage Using a Programmable Optical Mask in A Dispersive Flat-Field Near-Infrared Spectrometer.

Omar S. Khalil, Clinical Chemistry 45:2 (1999) pp. 165-177, entitled: Spectroscopic and Clinical Aspects of Noninvasive Glucose Measurements.

Omar S. Khalil, Diabetes Technology & Therapeutics, vol. 6, No. 5, 2004, Mary Ann Liebert, Inc. pp. 660-697, entitled: Non-Invasive Glucose Measurement Technologies: An Update From 1999 to the Dawn of the New Millennium.

Abraham Lorber, Analytical Chemistry 1986, 58, pp. 1167-1172, entitled Error Propagation and Figures of Merit for Quantification by Solving Matrix Equations.

Joseph Medendorp and Robert A. Lodder, Journal of Chemometrics (2005) 19: 533-542, entitled: Applications of Integrated Sensing and Processing in Spectroscopic Imaging and Sensing.

M.L. Myrick, O. Soyemi, H. Li, Zhang D. Eastwood, Fresenius J. Anal Chem (2001 369: 351-355, entitled: Spectral Tolerance Determination For Multivariate Optical Element Design.

Jonathon T. Olesberg, Mark A. Arnold, Carmen Mermelstein, Johannes Schmitz, and Joachim Wagnes, Applied Spectroscopy, vol. 59, No. 12, 2005, page Nos. 1480-1484, entitled: Tunable Laser Diode System for Noninvasive Blood Glucose Measurements.

Jonathan T. Olesberg, Lingzhi Liu, Valierie Van Zee, and Mark A. Arnold, Anal. Chem. 2006, 78, 215-233, entitled: In vivo Near-Infrared Spectroscopy of Rat Skin Tissue with Varying Blood Glucose Levels.

Vidi Saptari and Kamal Youcef-Toumi, Applied Optics/vol. 43, No. 13/May 1, 2004, entitled: Design of a Mechanical-Tunable Filter Spectrometer For Noninvasive Glucose Measurement.

International Search Report dated Sep. 25, 2007.

AM Glicksman (1963) An Introduction to linear programming and the theory of games. London, John Wiley and Sons.

P. Geladi & BR Kowalski,(1986) Partial Least-squares regression: a tutorial, Analytica Chimica Acta 185 1-17.

Johnson, RA & Wichem DW (1982) Applied multivariate statistical analysis. 3rd edition. Prentice Hall, Englewood Cliffs NJ. pp. 356-492.

* cited by examiner

METHOD AND DEVICE FOR ANALYTE MEASUREMENT

CROSS-REFERENCE TO RELATED APPLICATIONS

This application is based on and claims the benefit of U.S. Provisional Application No. 60/775,820, filed on Feb. 22, 2006 and entitled "METHOD AND DEVICE FOR ANALYTE MEASUREMENT," which is incorporated herein by reference in its entirety.

BRIEF DESCRIPTION OF THE DRAWINGS

The features and inventive aspects of the present invention will become more apparent upon reading the following detailed description and drawings. In the drawing figures, which are merely illustrative, and wherein like reference numerals depict like elements throughout the several views.

DETAILED DESCRIPTION

Figure 1:
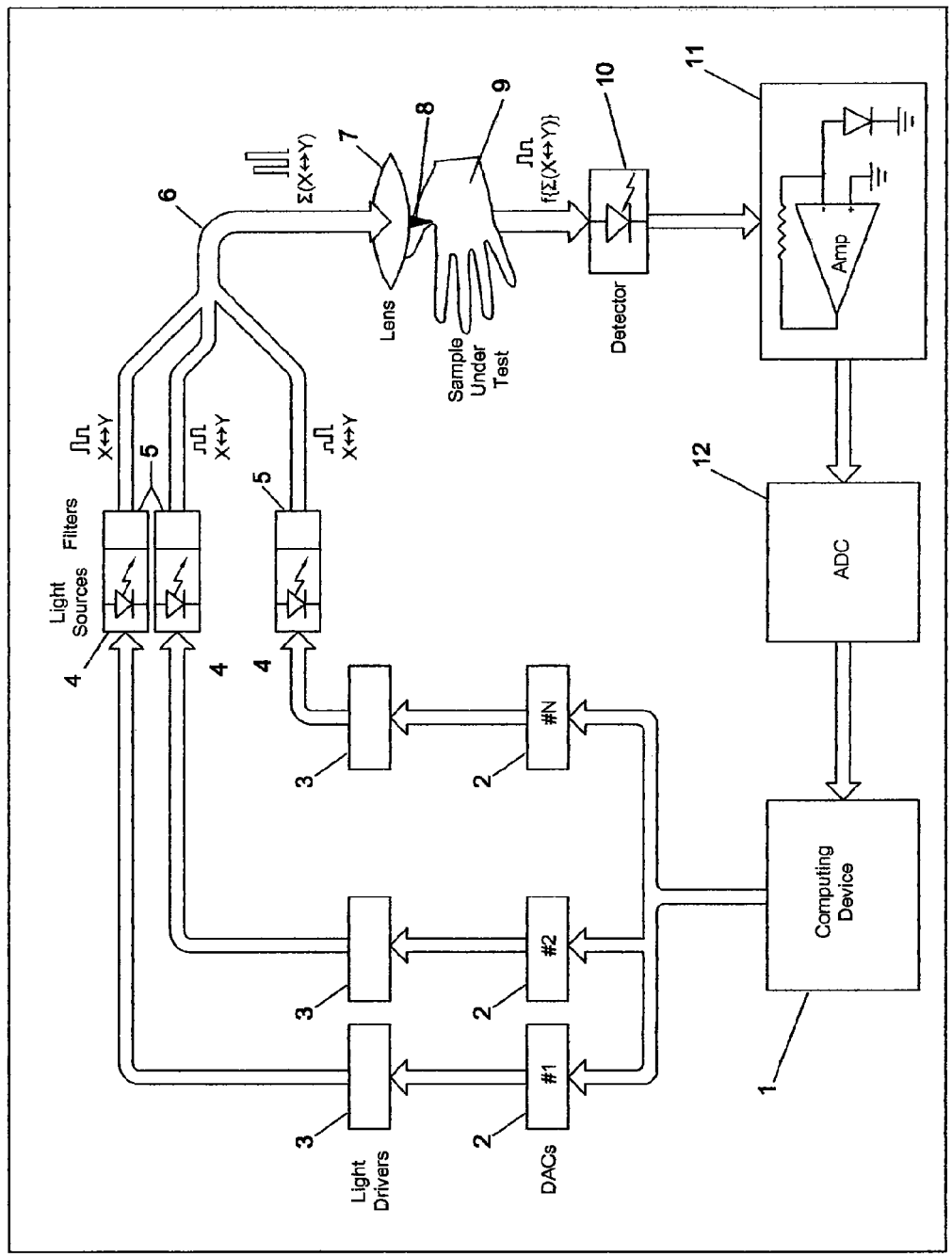
FIG. 1 is a block diagram according to an embodiment of the invention.

A device for measuring the concentration of one or more analytes consists of several light sources, a system for controlling the timing and intensity of the light sources' lights, a system for passing the light through the subject, a system for measuring the amount of light transmitted through the subject, and a system for relating the measurement to the concentration of the analyte in question. The light sources are narrow band sources at different wavelengths, and are capable of being rapidly switched between two levels of intensity. In one embodiment, the number of sources will be as few as four, but twenty-four or more sources may be required for some applications. The actual number of light sources required and the wavelengths of the sources are dependent upon the specific analyte being measured.

The systems referred to are composed of specific hardware controlled by software algorithms, and are described below. The intensity and timing control system converts a digital representation of a set of desired light levels into actual levels of light output, using digital to analog (DAC) circuitry under the control of a computer or embedded microprocessor using suitable calibration algorithms. Alternatively, pulse width modulation might be used in place of intensity control. The light control system uses optical means such as mirrors, lenses and/or fiber optics to gather the light from multiple light sources into a combined beam to arrive at the subject or sample under test. The light measurement system uses a photodetector, which converts transmitted or reflected light energy to electrical current, and a measurement circuit, which can thereby precisely measure the light impinging on the detector during multiple predetermined time periods. Finally the system for concentration measurement infers the concentration of the analyte of interest from the time-averaged light signal, using the mathematical theory of orthogonal vectors. Various embodiments of these systems are described below.

In one embodiment, at least 24 sources are used to measure the concentration of an analyte of medical interest in a biological tissue sample or a fold of skin. When suitable control algorithms are used, this large number of sources supports the ability to accurately measure target analytes in the presence of widely varying optical properties. Since living tissue will show biological variation and will scatter light randomly, this ability is important for in vivo measurements. Because the light beam from combined multiple sources will never have ideal properties, and because scattering within the sample will be unpredictable from one sample to another, simple measurements of the light attenuation from each individual source may not give reliable measurements of a target analyte concentration. However, with a sufficient number of sources, optical measurements of beam and sample inhomogeneity may be added as additional constraints in the Net Analyte Signal (NAS) calculation. A larger number of sources also increases selectivity relative to a target analyte and confers the ability to reprogram the NAS for different analytes. In an embodiment of the invention designed for analyte concentration measurements in vivo, the number of sources greatly exceeds the number of potentially interfering substances, but the device is programmed to compensate for sample inhomogeneity, and may be re-programmed for different analytes.

As shown in FIG. 1, a computing device that may be either a computer or an embedded microprocessor 1 is employed to control the light intensity emitted from each light source 4 in each of two intensity levels. Numerical values are sent from the computer 1 to several digital to analog converters (DACs) 2. The voltage output of the DACs is further converted (by light driver circuits) 3 into a current that is used to drive the light sources 4. The light sources 4 are narrow band sources, each at a different wavelength. Optical band pass filters 5 are employed to narrow the range of wavelengths from some or all of the sources. Various optical devices (such as optical fibers) 6 converge the several light beams into a single beam 8. A lens 7 focuses the single beam 8 onto the surface of the sample under test 9.

After passing through the sample under test 9, the light is directed onto a detector 10 that produces an electrical signal proportional to the intensity of the light. An amplifier 11 increases the level of the electrical signal that is then converted into a numerical value by an analog to digital converter (ADC) 12 and returned to the computer 1.

The computer 1 or an additional timer alternately switches the intensity of each light source between two different, predetermined levels, designated X and Y. The light switching is synchronous, so that at any point in time, either all of the sources will be in state X, or all of the sources will be in state Y In general, the difference between the X and Y levels of each source will be different from the difference between the X and Y levels of all other sources.

It follows, then, that the combined beam will also switch between the two states. In either state, the intensity of the combined beam will be the sum of the intensities of all of the individual beams in that state.

The combined light beam will be attenuated by the extent to which each individual wavelength has been absorbed by the various substances contained in sample. If the light intensities for both states of each light source have been set correctly, there will be a large difference (between the two states) if, and only if, one particular substance is present. If that substance is not present, the difference signal will be close to zero. The magnitude of the difference will be a function of the concentration of the substance of interest. In the absence of that substance, the output will be a constant level.

After a sufficient number of measurements have been performed, the computer 1 calculates and displays the concentration of the substance in question.

1. Hardware

Figure 2A:
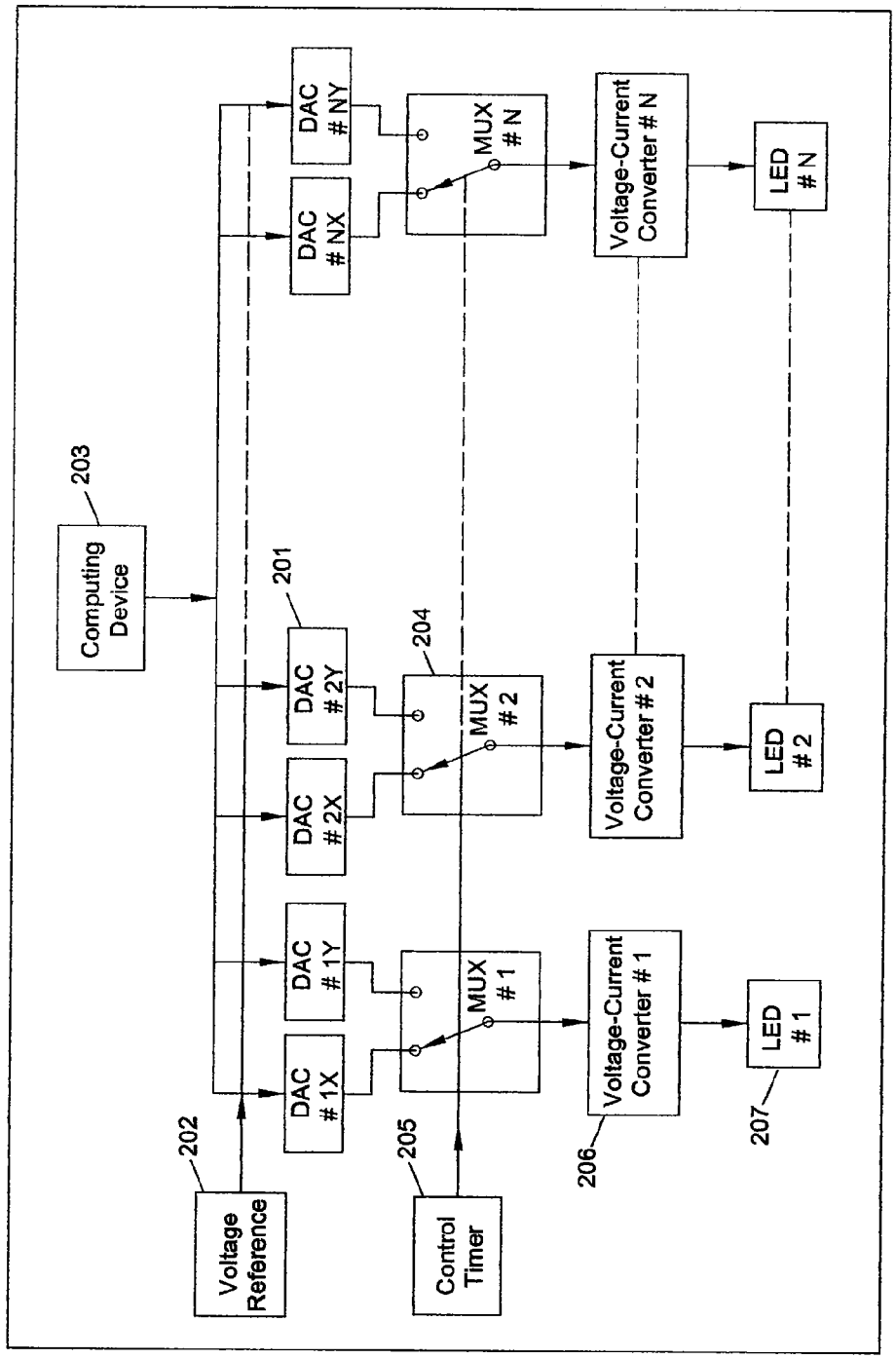
FIG. 2A illustrates one embodiment of a system for controlling the light levels for the light sources.

FIG. 2A illustrates a method of generating and controlling the required light beams. In this embodiment, there are two 16-bit digital to analog converters (DACs) 201 for each light source. The outputs of the DACs are controlled by a voltage reference 202 and a computing device 203. One multiplexer (MUX) 204 per light source and a timing circuit 205 are employed to switch the voltage to current converter light driver circuits 206 between the two DACs. Light emitting diodes (LEDs) 207 connected to the light driver circuits each emit a light beam that alternates between two different intensities.

Figure 2B:
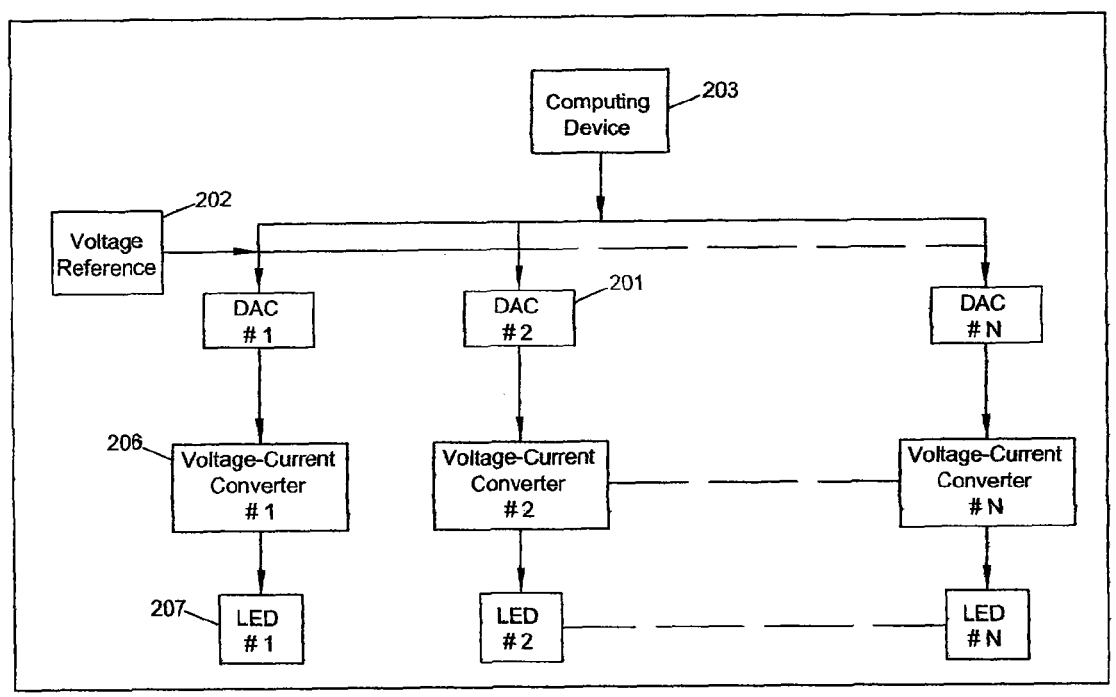
FIG. 2B illustrates an alternate embodiment of a system for controlling light levels for the light sources.

FIG. 2B illustrates another embodiment, wherein there is a single DAC 201 for each light source. In this embodiment, the computing device 203 is employed both to set the DAC outputs and to switch them between the two required voltages. The remainder of the device is similar to that illustrated in FIG. 2A.

Figure 3A:
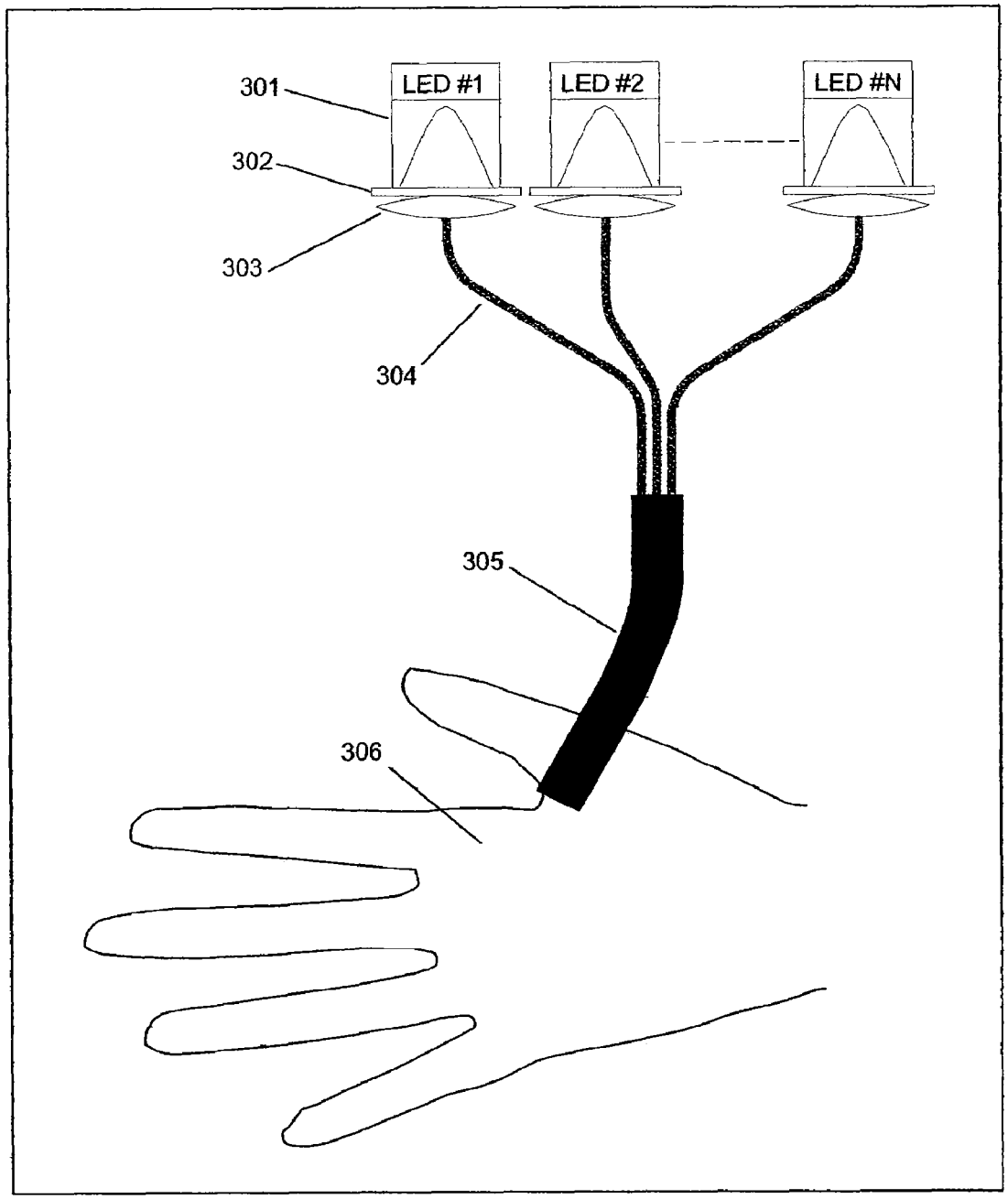
FIG. 3A illustrates one embodiment of a system for combining the several light beams and focusing them onto the sample under test.

FIG. 3A illustrates an embodiment in which the light sources are near infrared light emitting diodes (NIR LEDs) 301 with parabolic reflectors, and wavelengths ranging from 2000 nm to 2400 nm. In other embodiments, LEDs with longer or shorter wavelengths are employed. In another embodiment, laser diodes are used as the light sources. In one preferred embodiment, optical band pass filters 302 are employed to narrow the range of wavelengths from some or all of the sources. Where filters are used, the bandwidth is limited such that the full width half maximum is less than 100 nm. Lenses 303 are employed to focus the light from each LED onto a suitable optical fiber 304. The fibers from each LED are combined into a fiber bundle 305 that illuminates the sample under test 306 with a combined light beam. A Winston cone (not illustrated) or other non-imaging concentrator known to those skilled in the art may be used as light concentrators to couple the light source to the fiber optic bundle. The sample under test may be a portion of the human body or a material contained in a cuvette or other suitable transparent container.

The thickness of the sample under test will be limited by the ability of the specific wavelengths employed to penetrate the sample. For example, with wavelengths ranging from 2000 nm to 2400 nm human tissue as the sample will have a maximum practical thickness of approximately 1 to 4 mm. Suitable samples include the web of skin between the thumb and fore finger, the ear lobe, a skin fold, the cheek, the tongue, or other similar locations.

One embodiment of the invention for measuring glucose concentration, in the presence of a limited number of interfering analytes uses six near infrared light emitting diodes and six band pass filters, as indicated in Table 1. Someone skilled in the art will recognize that additional wavelengths will be required to differentiate glucose from a larger number of interfering analytes. It should also be recognized that substances other than glucose might require a totally different set of sources and filters.

TABLE 1

| Source | LED | | Filter | |
| --- | --- | --- | --- | --- |
|  | Center Wavelength | Full Width Half Maximum | Center Wavelength | Full Width Half Maximum |
| 1 | 2100 nm | 200 nm | 2117.5 nm | 10 nm |
| 2 | 2200 nm | 200 nm | 2195.0 nm | 43 nm |
| 3 | 2300 nm | 200 nm | 2290.0 nm | 10 nm |
| 4 | 2200 nm | 200 nm | 2248.0 nm | 27 nm |
| 5 | 2200 nm | 200 nm | 2162.5 nm | 30 nm |
| 6 | 2200 nm | 200 nm | 2217.5 nm | 25 nm |

Figure 3B:
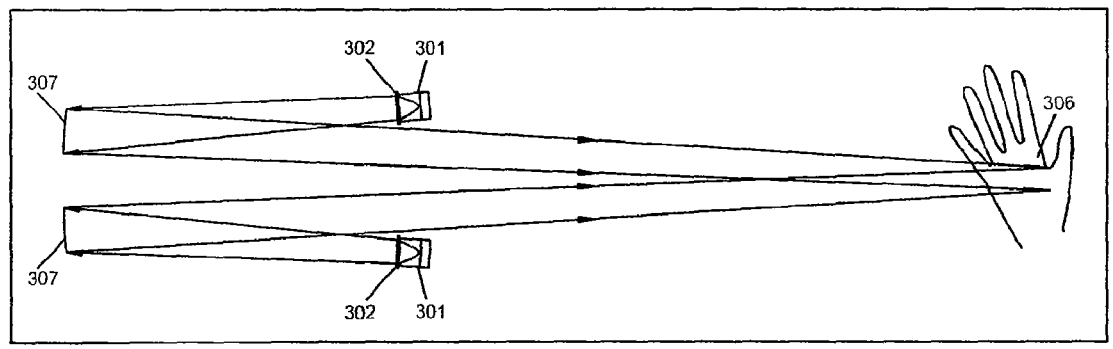
FIG. 3B illustrates another embodiment of a system for combining and focusing the light beams.
Figure 3C:
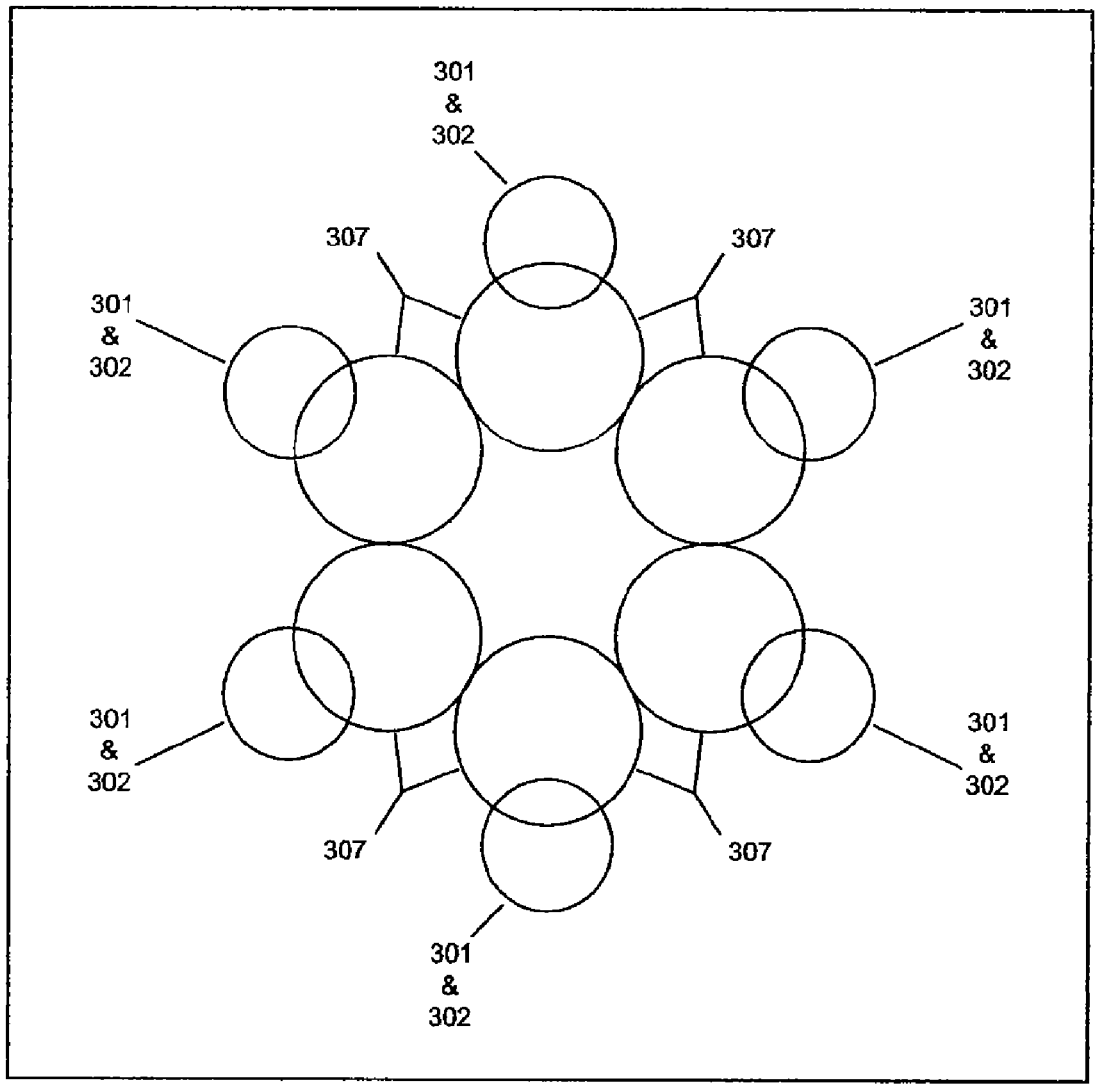
FIG. 3C illustrates another view of the embodiment of the system in FIG. 3B.

FIGS. 3B and 3C illustrate another method of combining any of the multiple light sources and filters (described above) into a single beam and directing the beam onto the surface of the sample under test. Each light source is directed at a spherical mirror 307 that condenses the beam and directs it onto the sample. The mirrors are all in the same plane and arranged in a circle. The sources are arranged in a larger circle with the reflected beam passing through the center of the circular array of detectors. The arrangement illustrated in FIG. 3C is for six sources and six mirrors, but other numbers are equally possible.

Figure 4A:
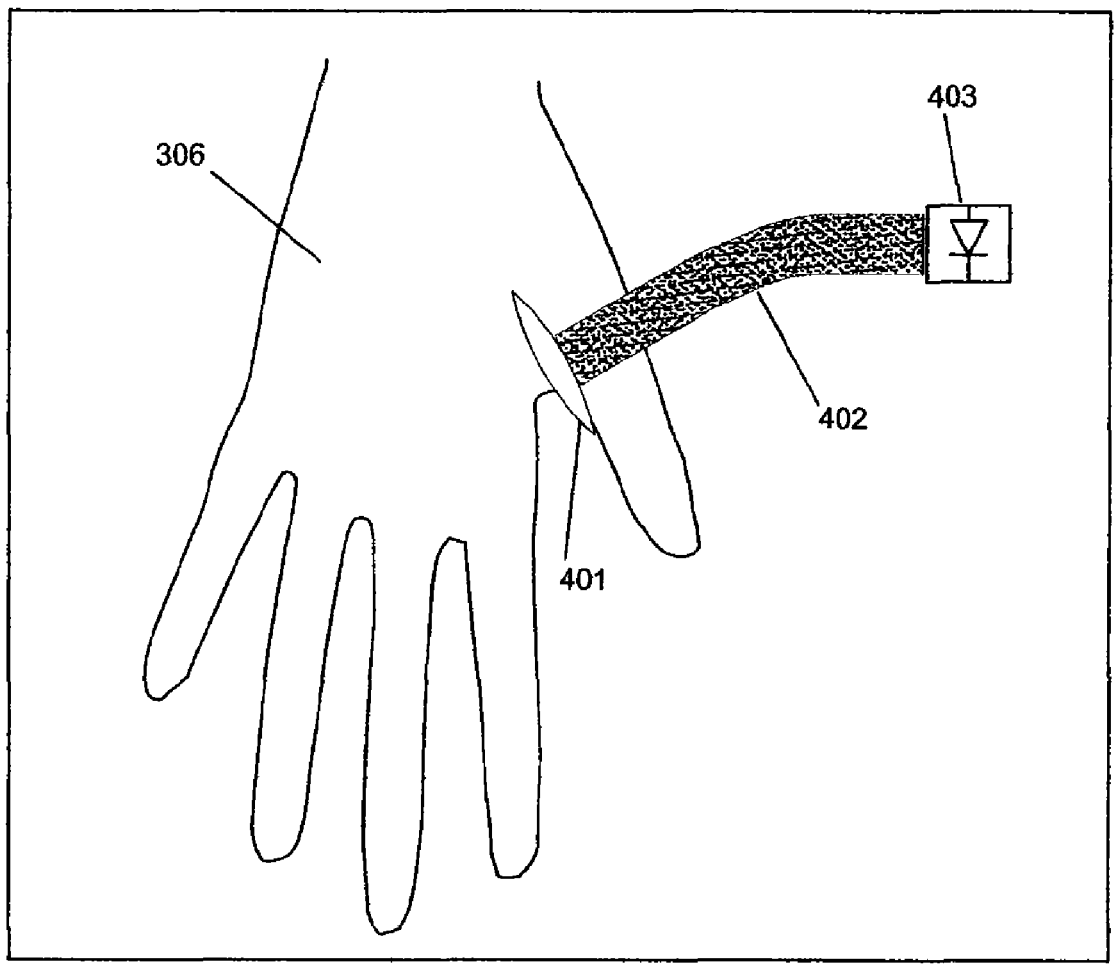
FIG. 4A illustrates one embodiment of a system for focusing the light beam onto a detector.

FIG. 4A illustrates a method of collecting the light that has passed through the sample under test 306 and focusing it onto the detector. A lens 401 focuses the light onto one end of a fiber optic bundle 402. The fiber optic bundle may be comprised of multiple fibers or may be a single fiber. The other end of the fiber optic bundle is directed onto a detector 403 that is suitable for the range of wavelengths contained in the beam. A Winston cone (not illustrated) or other non-imaging concentrator may be used as a light concentrator to couple the fiber optic bundle to the detector. In the embodiment that uses wavelengths in the range of 2000 nm to 2400 nm, the detector may be an indium gallium arsenide photodiode. In other wavelengths, photodiodes of other materials, photo multiplier tubes, or other types of light detectors may be substituted.

Figure 4B:
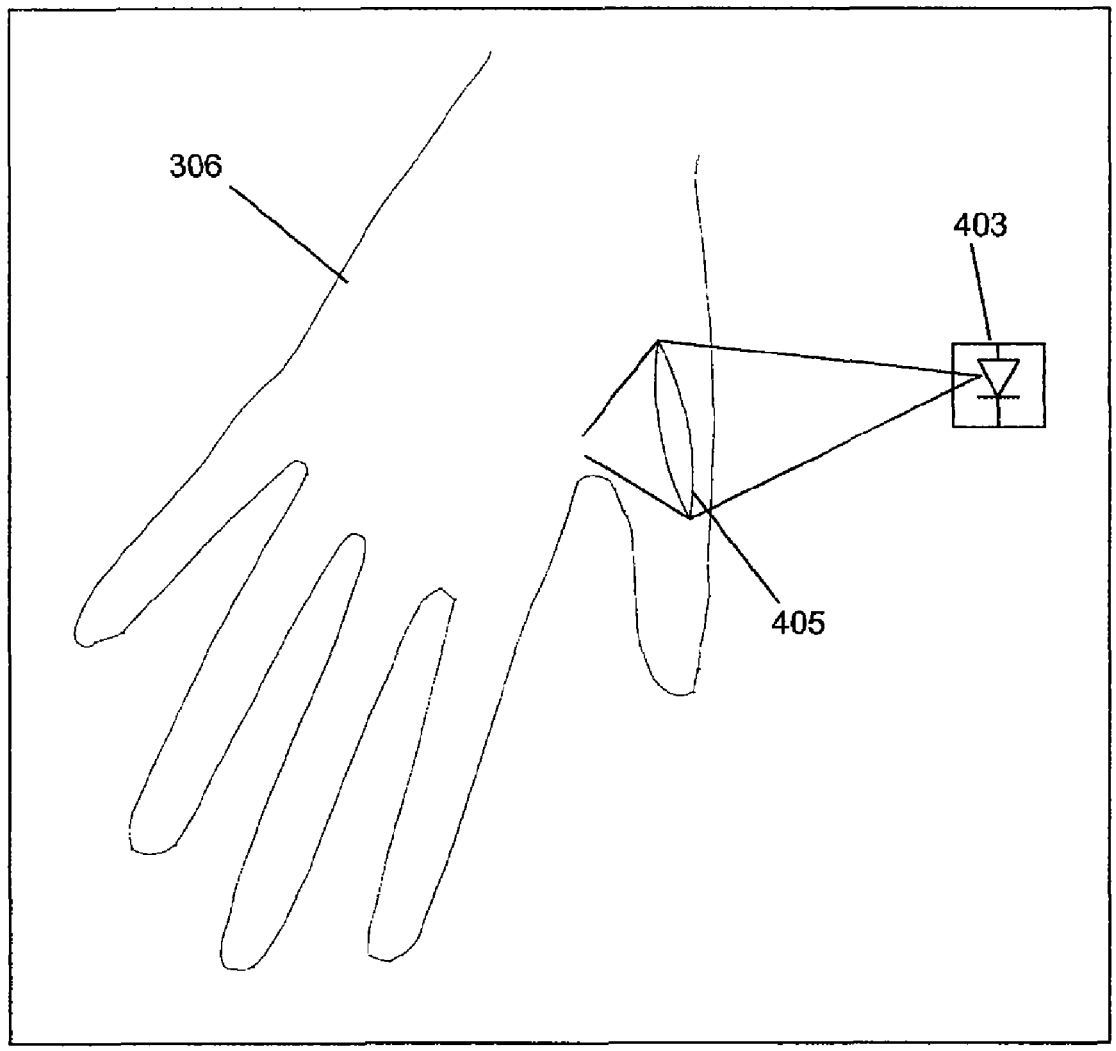
FIG. 4B illustrates another embodiment of a system for focusing the light beam onto the detector.
Figure 4C:
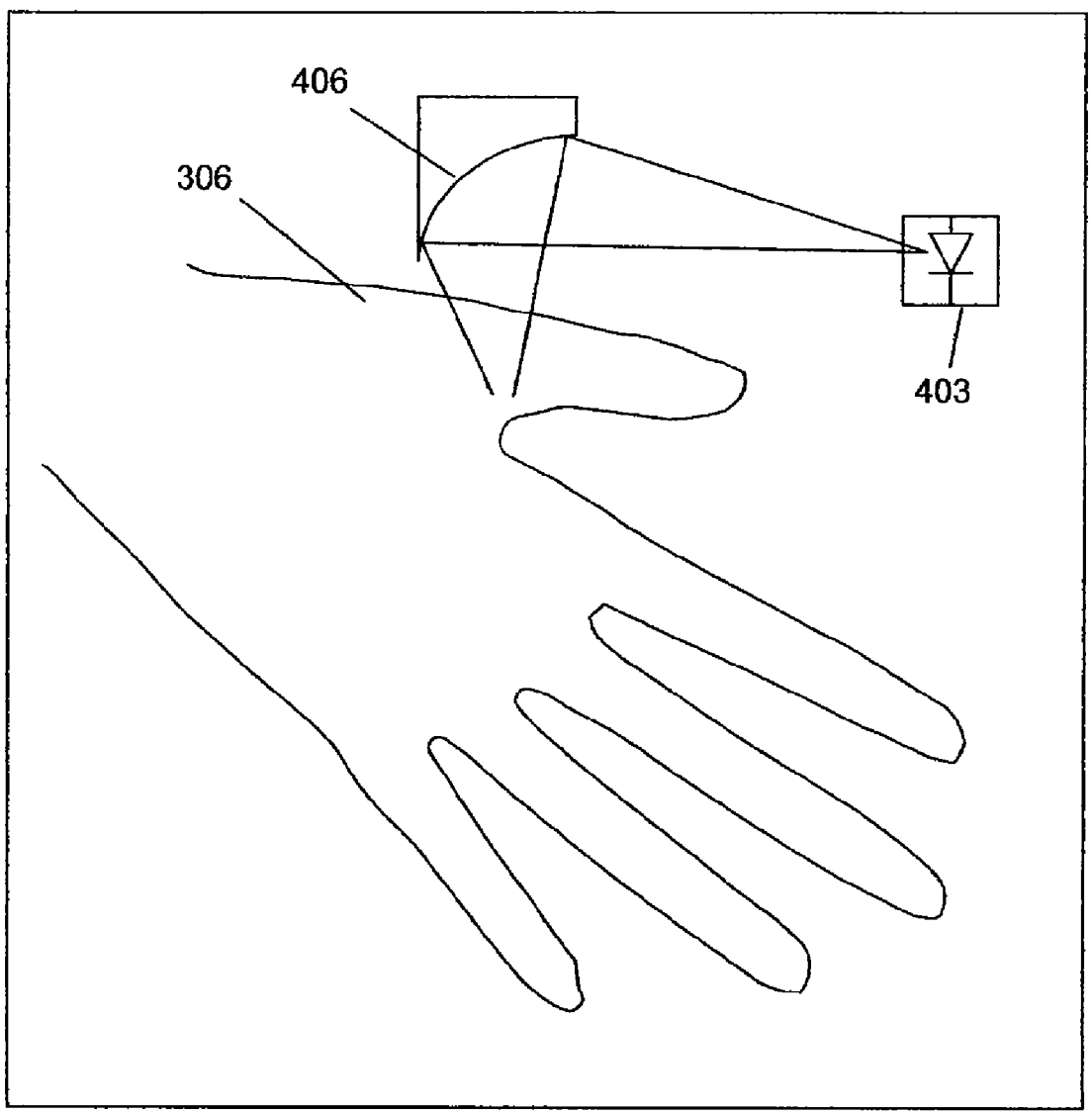
FIG. 4C illustrates yet another embodiment of a system for focusing the light beam onto a detector.

FIGS. 4B and 4C illustrate two other embodiments wherein one embodiment, a lens 405 is used and in the other embodiment an off axis parabolic mirror 406 is used to focus the emerging light beam onto the detector described above.

Figure 5A:
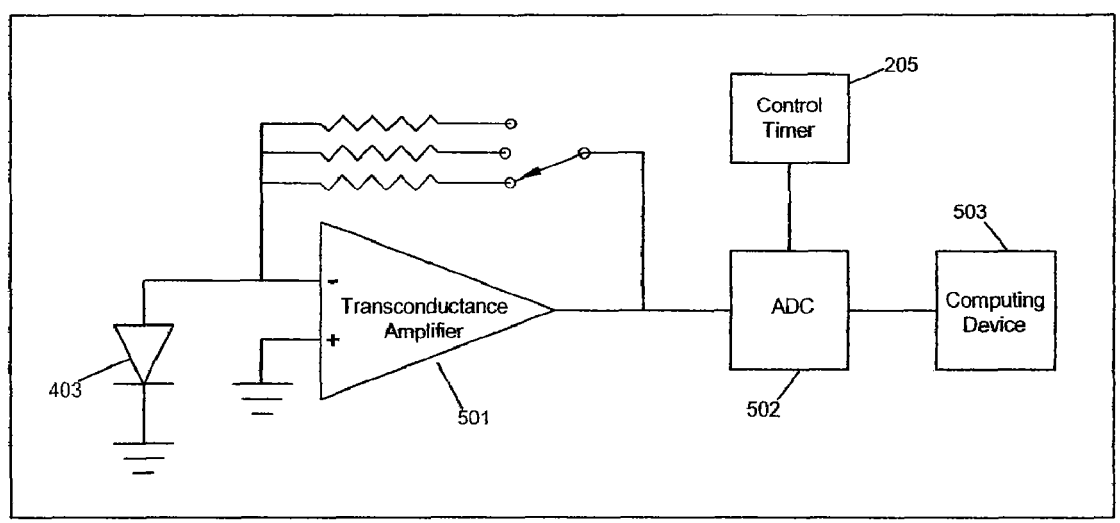
FIG. 5A illustrates an embodiment of a system for digitizing the signal output from a detector.

There are many possible methods available to digitize the signal from the detector. In FIG. 5A the detector 403 is connected to a transconductance amplifier 501. The output of the amplifier is connected to a high-speed analog to digital converter (ADC) 502 such as a delta sigma converter. In order to achieve the required degree of precision, the ADC should be capable of at least 20 bits of resolution. The ADC is controlled by the same timing circuit 205 that controls the light levels. The output of the ADC is transmitted to the computing device 503 that is either a computer or a dedicated microprocessor. In this configuration, the light sources are switched to state X, and the detector output is digitized and recorded. The sources are then switched to state Y and the detector output is again digitized and recorded. This sequence is repeated several times at a rate of approximately 1 kHz. The resulting signal is the difference between the average X value and the average Y value.

Figure 5B:
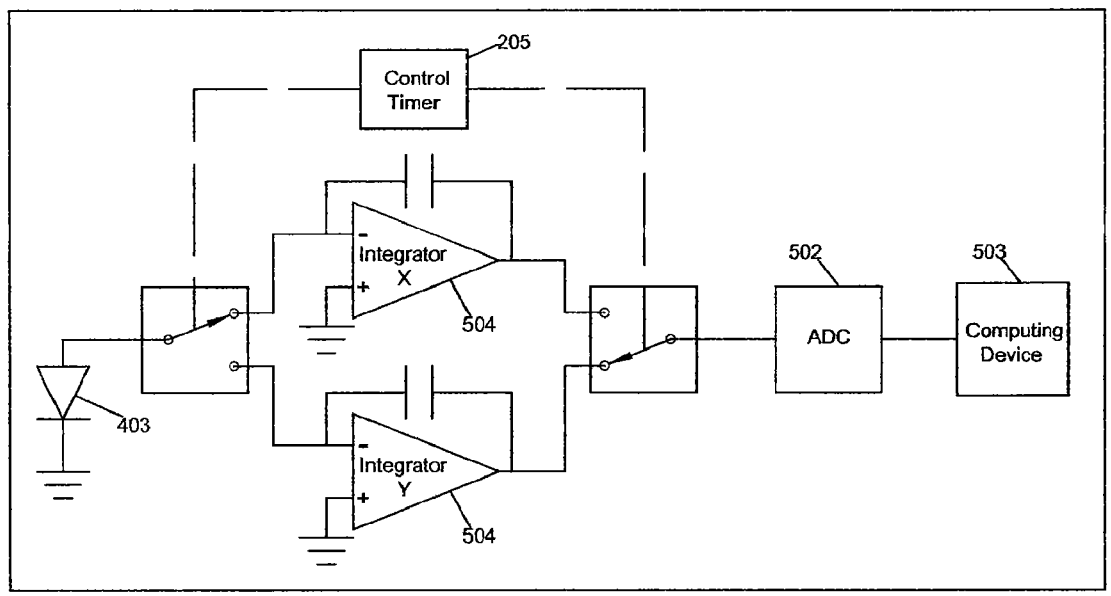
FIG. 5B illustrates an alternate embodiment of a system for digitizing the signal output from a detector.

Another embodiment is illustrated in FIG. 5B. Here, the detector is alternately switched between two integrating charge amplifiers 504. The outputs of the integrators are alternately switched to an ADC similar to that illustrated in FIG. 5A. The output of the ADC is connected either to a computer or to a dedicated microprocessor. The integrator switching, the ADC, and the discharging of the integration capacitors is controlled by the same timing circuit 205 that controls the light levels. In this configuration, the light sources are switched to state X, and the detector output is connected to integrator X. At the same time, the output of integrator Y is connected to the ADC. Once the analog to digital conversion is completed, the result is stored in the computing device. Integrator Y is then reset by discharging the integrating capacitor. After the entire X pulse has been integrated, the timing circuit switches the lights to state Y, connects the detector to integrator Y, and connects integrator X to the ADC. This sequence is repeated several times. As with the previous configuration, the switching rate is approximately 1 kHz. The resulting signal is the difference between the average X value and the average Y value.

Figure 5C:
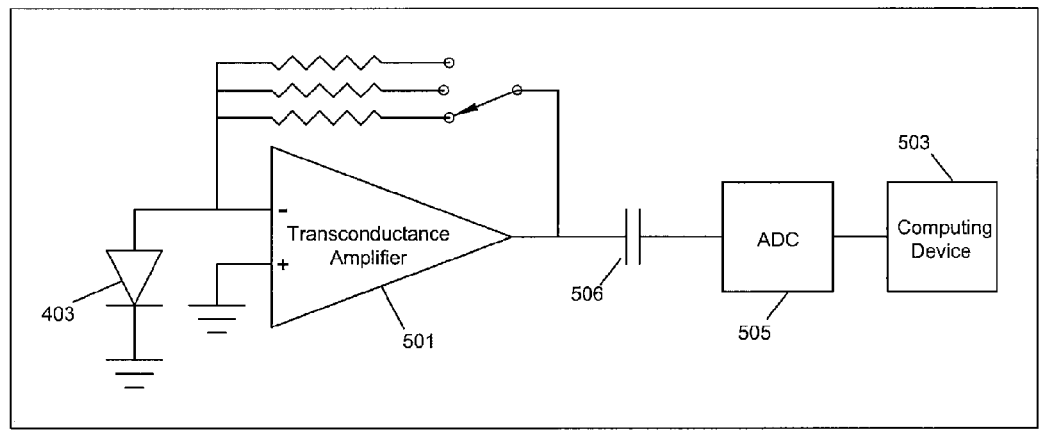
FIG. 5C illustrates another alternative embodiment of a system for digitizing the signal output from a detector.
Figure 5D:
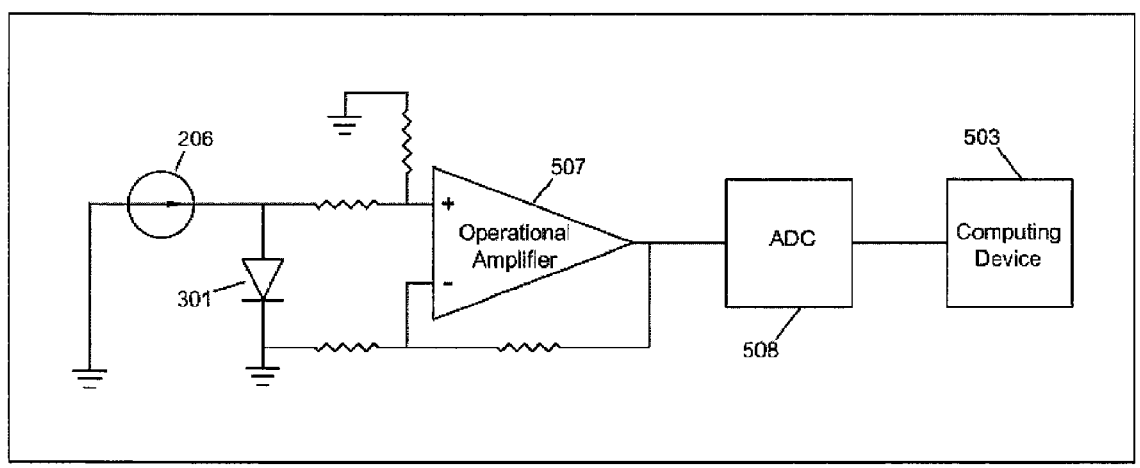
FIG. 5D illustrates an embodiment of a system for measuring the temperature of light sources.

Yet another embodiment is illustrated in FIG. 5C. In this configuration, the output of the detector is connected to a transconductance amplifier similar to that illustrated in FIG. 5A. The amplifier is AC coupled to an ADC 505 through a capacitor 506. Here, the ADC is a slow averaging type such as a dual slope converter capable of at least 20-bit precision. The AC coupling causes the difference between the X and Y states to appear in a single measurement on the ADC. This circuit will give best results if the switching between the states is at a rate from 10 kHz up to several MHz. The dual slope converter will yield good average measurements without the need to average many readings FIG. 5D illustrates an embodiment in which the junction temperature of the near infrared light emitting diodes (NIR LEDS) 301 is measured. The current source 206 may be any of the voltage to current converter light driver circuits 206 described in FIG. 2A or 2B. An operational amplifier 507 detects the voltage drop across the diode junction. The voltage drop is digitized by an analog to digital converter (ADC) 508 that is independent from the ADC in FIGS. 5A through 5C. The digitized voltage drop is fed into the computing device 503 for further processing.

2. Operation

Figure 6:
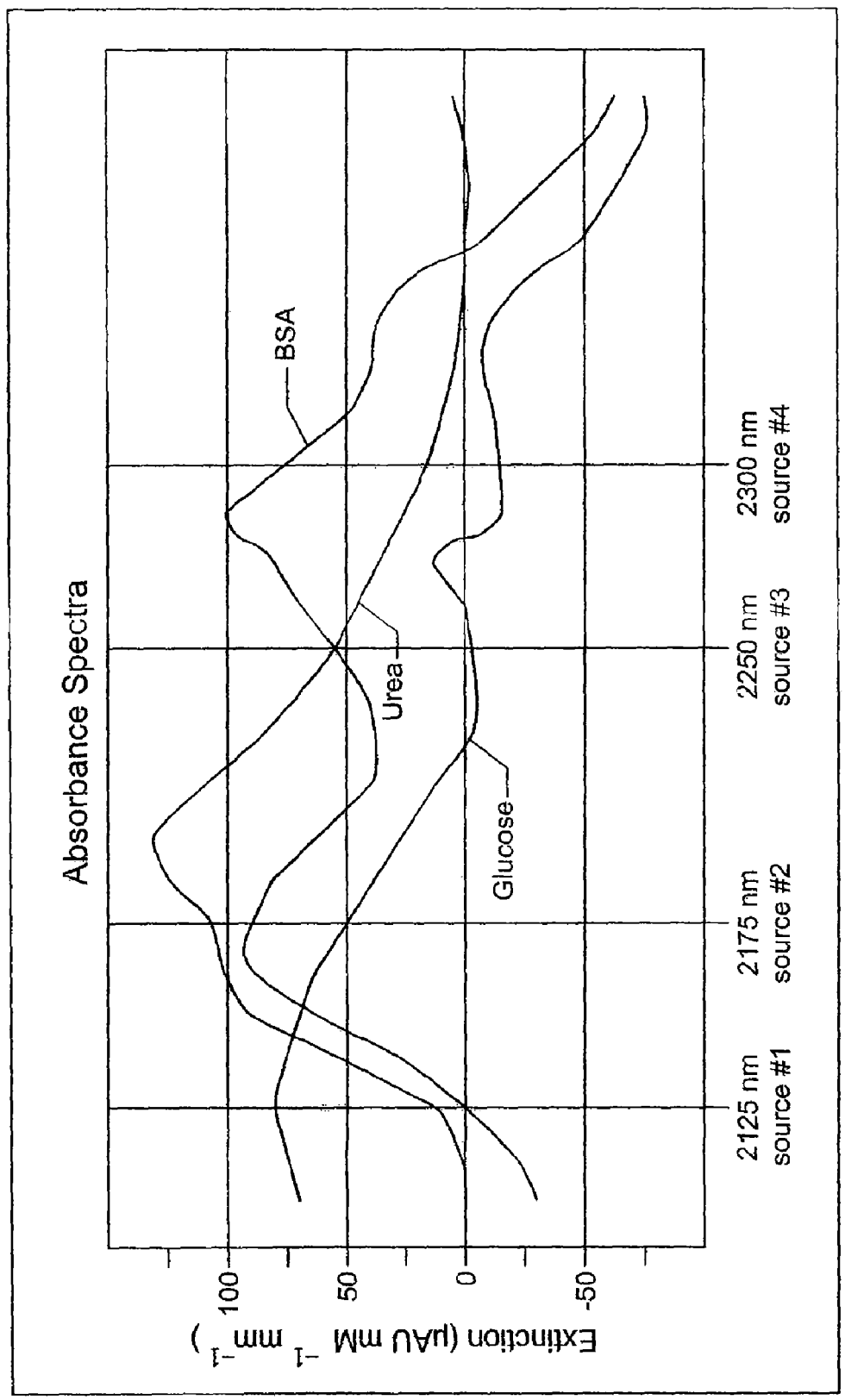
FIG. 6 illustrates absorption spectra for three different analytes.

FIG. 6 illustrates the absorption spectra (in water) for glucose, urea, and bovine serum albumin (BSA) for light in the range of 2100 nm to 2400 nm. Consider a device with four light sources. One at 2125 nm, one at 2175 nm, one at 2250 nm, and one at 2300 nm. The % attenuation can be calculated from the curves in FIG. 6 by the formula $\alpha_\lambda = 100*(1-10^{-B*C*L/1,000,000})$, where a is the % attenuation at wavelength $\lambda$, B is the extinction coefficient (in micro absorbance units) for each substance, at wavelength $\lambda$, C is the concentration in milliMoles per liter (mM), and L is the path length in mm. Table 2 lists the attenuation due to each substance at those wavelengths.

TABLE 2

% Attenuation through 1 mm with 50 mM Concentration

|  | 2125 nm | 2175 nm | 2250 nm | 2300 nm |
| --- | --- | --- | --- | --- |
| Glucose | 0.917 | 0.574 | −0.035 | −0.167 |
| Urea | 0.0 | 1.03 | 0.631 | 0.871 |
| BSA | 0.144 | 1.22 | 0.631 | 0.184 |

By judiciously setting the light intensities, it is possible to make the device highly sensitive to one substance and essentially insensitive to the other substances. A particular set of levels is referred to as a NAS. Table 3A lists the settings of these sources for a Glucose NAS.

It should be noted that traditional spectrographic analysis uses a slightly different meaning for NAS. Although we have borrowed the term, this technique sufficiently departs from traditional methods that a different definition is required. In the traditional meaning, NAS is an output or result. It refers to specific linear combination of the measured absorption values of several different wavelengths. In the meaning employed here, NAS is an input. It refers to the two state (X and Y) intensity settings of each of several different wavelengths.

TABLE 3A

Light Intensities for Glucose NAS

|  | 2125 nm | 2175 nm | 2250 nm | 2300 nm |
| --- | --- | --- | --- | --- |
| State X | 355 | 443 | 0 | 197 |
| State Y | 0 | 0 | 995 | 0 |

The amount of light transmitted at each wavelength can be described by the formula $T_\lambda = S_\lambda \cdot (1 - A_{s1\lambda} - A_{s2\lambda} - A_{s3\lambda})$ where $T_\lambda$ is the light transmitted at wavelength $\lambda$, $S_\lambda$ is the source intensity at wavelength $\lambda$, and $A_{s1\lambda}$ through $A_{s3\lambda}$ are the absorptions of substances 1 through 3 at wavelength $\lambda$. The absorptions are computed by $A_{si\lambda} = \alpha_{si\lambda}/100$. In each state, the total transmitted light ($T_{TX}$ and $T_{TY}$) will be the sum of the $T_\lambda$ values for all four wavelengths. Because only the difference between the two states is significant, the total amount of power required can be minimized by arbitrarily setting one state of each source to zero.

The calculated light transmission signals for the Glucose NAS are indicated in Table 3B. The significant numbers are the total differences ($\Delta$s) between the X and Y states. These differences can be thought of as the real signal. With no substances present, there is no absorption, and all of the light is transmitted. It is important to note that because this NAS is designed to measure glucose concentration, the presence of urea, BSA, or both urea and BSA result in essentially zero signal. Equally important is the fact that the presence of urea and/or BSA has essentially no effect on the relatively high signal when glucose is present. Clearly, the signal is dependent upon the presence and concentration of glucose, and independent of the other analytes.

TABLE 3B

Transmitted Light Through 1 mm with Glucose NAS

| Analyte(s) Present | | 2125 nm | 2175 nm | 2250 nm | 2300 nm | Total |
| --- | --- | --- | --- | --- | --- | --- |
| None | X | 355.000 | 443.000 | 0.000 | 197.000 | 995.000 |
|  | Y | 0.000 | 0.000 | 995.000 | 0.000 | 995.000 |
|  | Δ |  |  |  |  | 0.000 |

TABLE 3B-continued

Transmitted Light Through 1 mm with Glucose NAS

| Analyte(s) Present | | 2125 nm | 2175 nm | 2250 nm | 2300 nm | Total |
|---|---|---|---|---|---|---|
| 25 mM of | X | 353.372 | 441.729 | 0.000 | 197.165 | 992.266 |
| Glucose only | Y | 0.000 | 0.000 | 995.174 | 0.000 | 995.174 |
| | Δ | | | | | 2.908 |
| 50 mM of | X | 351.745 | 440.457 | 0.000 | 197.329 | 989.531 |
| Glucose only | Y | 0.000 | 0.000 | 995.348 | 0.000 | 995.348 |
| | Δ | | | | | 5.817 |
| 50 mM of | X | 355.000 | 438.437 | 0.000 | 195.284 | 988.721 |
| BSA only | Y | 0.000 | 0.000 | 988.722 | 0.000 | 988.722 |
| | Δ | | | | | 0.001 |
| 50 mM of | X | 354.489 | 437.595 | 0.000 | 196.638 | 988.722 |
| Urea only | Y | 0.000 | 0.000 | 988.722 | 0.000 | 988.722 |
| | Δ | | | | | 0.000 |
| 50 mM each of | X | 354.489 | 433.033 | 0.000 | 194.922 | 982.444 |
| BSA and Urea | Y | 0.000 | 0.000 | 982.443 | 0.000 | 982.443 |
| | Δ | | | | | 0.001 |
| 50 mM each of | X | 351.233 | 430.490 | 0.000 | 195.251 | 976.974 |
| Glucose, BSA, and Urea | Y | 0.000 | 0.000 | 982.791 | 0.000 | 982.791 |
| | Δ | | | | | 5.817 |

With exactly the same light sources, but different light levels, a NAS for many other substances can be set. Table 4 lists the NAS for urea.

TABLE 4

Light Intensities for Urea NAS

| | 2125 nm | 2175 nm | 2250 nm | 2300 nm |
|---|---|---|---|---|
| State X | 0 | 176 | 991 | 0 |
| State Y | 241 | 0 | 0 | 926 |

The calculated results for the Urea NAS are listed in Table 5. Here, we see that the signal is dependent upon the presence and concentration of urea, and independent of the other analytes.

TABLE 5

Transmitted Light With Through 1 mm with Urea NAS

| Analyte(s) Present | | 2125 nm | 2175 nm | 2250 nm | 2300 nm | Total |
|---|---|---|---|---|---|---|
| None | X | 0.000 | 176.000 | 991.000 | 0.000 | 1167.000 |
| | Y | 241.000 | 0.000 | 0.000 | 926.000 | 1167.000 |
| | Δ | | | | | 0.000 |
| 25 mM of | X | 0.000 | 174.926 | 987.873 | 0.000 | 1162.799 |
| Urea only | Y | 240.827 | 0.000 | 0.000 | 925.148 | 1165.975 |
| | Δ | | | | | 3.176 |
| 50 mM of | X | 0.000 | 173.853 | 984.747 | 0.000 | 1158.600 |
| Urea only | Y | 240.653 | 0.000 | 0.000 | 924.296 | 1164.949 |
| | Δ | | | | | 6.349 |
| 50 mM of | X | 0.000 | 174.187 | 984.747 | 0.000 | 1158.934 |
| BSA only | Y | 241.000 | 0.000 | 0.000 | 917.935 | 1158.935 |
| | Δ | | | | | 0.001 |
| 50 mM of | X | 0.000 | 174.990 | 991.347 | 0.000 | 1166.337 |
| Glucose only | Y | 238.790 | 0.000 | 0.000 | 927.547 | 1166.337 |
| | Δ | | | | | 0.000 |
| 50 mM each of | X | 0.000 | 173.177 | 985.094 | 0.000 | 1158.271 |
| BSA and Glucose | Y | 238.790 | 0.000 | 0.000 | 919.481 | 1158.271 |
| | Δ | | | | | 0.000 |
| 50 mM each of | X | 0.000 | 171.030 | 978.840 | 0.000 | 1149.87 |
| Urea, BSA, and Glucose | Y | 238.443 | 0.000 | 0.000 | 917.777 | 1156.87 |
| | Δ | | | | | 6.350 |

It should be understood that the above description is greatly simplified for the purpose of explaining the method of operation. In the real world, the light sources may not be completely monochromatic. A typical sample (often, a part of the human body) will have far more than three substances present. There will likely be a significant amount of (highly attenuating) water present in the sample. Also, with these examples where the number of substances is the same as the number of wavelengths employed (no substance is essentially equivalent to having a fourth substance) the NAS is unique. If the number of wavelengths were to exceed the number of substances of interest, there will be many possible NAS sets for each substance.

Measurements of analytes in a tissue will require twenty-four or more different light sources, each at a different wavelength. Alternatively, a smaller number of sources capable of emitting light of controlled intensity and timing, each at multiple wavelengths, might be employed. Fortunately, the method described above can easily be extended to any number of wavelengths. The NAS of the light beam can be considered to be a vector in N dimensional space. For this example, the vector is 4 dimensional. For any N dimensional space, it is always possible to construct N mutually orthogonal vectors. An NAS vector for any one substance will be sensitive to that substance, and insensitive to all the other substances.

Measuring the absorption of light through a specimen gives information about the amount of analyte present. However, the concentration of an analyte is defined as the ratio of the analyte amount to the amounts of other substances, such as water. Therefore, going from glucose absorption to glucose concentration requires knowledge of the path length. The method described here contains a solution to this problem. By configuring a Water NAS it is possible to compute the ratio of glucose absorption to water absorption. This will directly yield a measurement of glucose concentration. The same method can be applied to yield the concentration of any other analyte.

3. Finding a NAS

In theory, there are an infinite number of NASs for any combination of substances. Some will work well, while others will not. The problem is to find a good one. The method of computing the NAS for any substance involves several steps. Some of the steps are quite rigorously defined, while some others will require a certain amount of intuition and trial and error testing or mathematical simulation. Good intuition will reduce the amount of trial and error testing, but will not eliminate it completely. Conversely, poor intuition will increase the amount of trial and error testing, but will not preclude achieving a workable NAS. Computer simulations can be applied to automate much of the initial testing.

The first step is to define the substance of interest and the environment in which the measurements will be made. A significant part of the definition of the environment will be an identification of the other substances that will be present and that may interfere with the measurement. For example, if the problem is to perform in vivo measurements of glucose in humans, then interfering substances will include (but certainly not be limited to) ascorbate, lactate, urea, alanine, triacetin, BSA (or HSA), water, etc. Some substances will be present, but may not be interfering. In this example, significant amounts of hemoglobin will be present. If the measurements will be performed above 2000 nm, hemoglobin will not interfere because it does not have significant absorption at those wavelengths. At shorter wavelengths, hemoglobin could potentially interfere, and would need to be considered.

The second step is to determine the absorption spectra of the substance of interest and all of the identified interfering substances. For wavelengths longer than about 1800 nm, the spectra for most common substances have been published and are readily available. For shorter wavelengths, the spectra may be more difficult to obtain. Standard methods for measuring spectra are well understood, and are outside the scope of this patent. For additional information, refer to "Substance spectrum tabulation" in "The Software," below.

The third step is to determine the number of different light sources, and to select their wavelengths. If there is no measurement error, the NAS calculation requires a number of light sources equal to at least two plus the number of interfering substances. In practice the number of sources required depends on the nature and size of the differences between the spectra of the target analyte and the interfering analytes, compared to the measurement error. If there is a wavelength where the absorption of the substance of interest is significantly different from that of an interfering substance, this wavelength is a good choice. A wavelength where the absorption of the substance of interest is different from that of several interfering substances is a better choice. Distributed small differences in the spectra may require more sources than large differences concentrated at a small set of wavelengths. More sources may be required because small differences in the spectra can only contribute a small amount to the NAS signal for each wavelength (source) used. Conversely, if there is a unique absorbing wavelength for the substance of interest, the NAS calculation becomes unnecessary. For additional information, refer to "Source selection" in "The Software" below.

The fourth step is to construct a set of k vectors in N dimensions, where k is the number of interfering substances and N is the number of discrete wavelengths (light sources) to be used. Each vector will represent the spectrum of a substance. The wavelengths will be directions in the N dimensional space, with the magnitude in each direction being the absorption of that substance at that wavelength.

The goal is to find a vector (the NAS) that is orthogonal to all of the other vectors. When N<k+2, there are no mathematical solutions to the problem. However it still may be possible to use one vector to represent several interfering substances if they are sufficiently similar on a judiciously chosen set of wavelengths. This strategy can sometimes reduce the effective value of k. In this case the choice of wavelengths is especially important and difficult. If N=k+2, there is an exact solution to the problem. However a larger number of sources N>k+2 can give a larger signal. When N>k+2, there are an infinite number of orthogonal vectors, and calculation of the NAS becomes more complicated. The NAS vector must be orthogonal to the interfering substance vectors but must also point, as much as possible, along the target analyte vector. A method to calculate a unique NAS for this case is now described.

Step five is to compute the NAS vector. Suppose we want to compute a vector w which is simultaneously orthogonal to a set of vectors (constraints) $u_i$, i=1, k but has a non-zero projection on a special direction v (the vector representing the substance of interest). The letter k now represents the number of interfering substances plus 1. Each vector has N components. Form a matrix $U_{k \times N}$ with rows $u_i$, i=1, k. The subscripts indicate that U has k rows and N columns. Then proceed as follows:

Define $R_{k \times 1}$=Uv. Each entry of the column vector R is the dot product of v and a row of U. For instance, for two vectors p and q, if p (1, 2, 3) and q (−1, −1, 1) then the dot product is p·q=1*(−1)+2*(−1)+3*(1)=−1−2+3=0. Any vectors are orthogonal if, and only if they have zero dot product.

Now solve for the vector X in the k equations given by:

$$UU^T x = -R;$$

where T is the operation of interchanging rows and columns (transpose) and the matrix $UU^T$ is k×k. To make $UU^T$, each column of $U^T$ is dotted into each row of U, to make a matrix that is formed from the dot product of each pair of the rows of U. Because $UU^T$ is a square matrix the equation is easy to solve. As an example:

$$\text{If } U = \begin{bmatrix} 1 & 2 & 3 & 7 \\ 4 & 5 & 6 & 8 \end{bmatrix} \text{ then } UU^T = \begin{bmatrix} 2 & 3 & 7 \\ 5 & 6 & 8 \end{bmatrix} \cdot \begin{bmatrix} 1 & 4 \\ 2 & 5 \\ 3 & 6 \\ 7 & 8 \end{bmatrix} =$$

$$\begin{bmatrix} 1*1+2*2+3*3+7*7 & 1*4+2*5+3*6+7*8 \\ 1*1+5*2+6*3+8*7 & 4*4+5*5+6*6+7*7 \end{bmatrix}$$

Then the vector $w = U^T x + v$ is the NAS vector that we want. Each light source will correspond to one element (dimension) of the vector. The difference between the two (X and Y) states of the light source will equal the magnitude of the corresponding vector element. The most efficient method (in terms of power consumption) is: for each positive element, set the X state of the corresponding light source equal to the element and set the Y state to zero. For each negative element, set the Y state of the light equal to the element and set the X state to zero. For additional information, refer to "NAS calculation" in "The Software," below in section 5.

The method described above to calculate the net analyte signal only uses information about the absorption spectra of the target and interfering analytes. These calculations will always produce a choice of light intensities that gives an AC signal as the apparatus is switched between the X and Y states when the target analyte is present, and little or no AC signal in response to other known analytes. However, when the number of sources with different wavelengths exceeds the number of analytes many different light intensity choices can satisfy these requirements. Some of these choices produce bigger signals than others. Thus, the method described above does not always produce the largest possible AC signal. When the concentration of the target analyte is small it is desirable to increase the signal size as much as possible. This can be done by using additional information about the relative light powers, which are available from each light source.

These powers can differ widely, since light from the sources may pass through optical filters of different transmissions and band pass characteristics. For example, if the available powers in arbitrary units follow Table 6, then a NAS may be calculated without using the data in Table 6, using the methods described earlier and the data in Table 2, for the absorption/transmission of glucose, urea and BSA. In this example, only urea and glucose are considered for simplicity of the illustration. In this case the NAS becomes as shown in Table 7A, which generates a NAS signal of 2.07, for 50 mM glucose. This signal is limited by the power available at 2125 nm, since no source can produce more than the power given in Table 6.

TABLE 6

Available Power

| | 2125 nm | 2175 nm | 2250 nm | 2300 nm |
|---|---|---|---|---|
| Power | 1 | 7 | 3 | 10 |

TABLE 7A

Light Intensities for Glucose NAS/Urea Scaled to Power

| | 2125 nm | 2175 nm | 2250 nm | 2300 nm |
|---|---|---|---|---|
| State X | 1 | 2.64 | 0 | 0 |
| State Y | 0 | 0 | 1.87 | 1.67 |

It is possible to obtain a bigger signal from a modified NAS obtained by systematically setting combinations of 2 out of 4 sources to their Table 6 values, and then using the constraints to fill in the remaining intensities. For example in the first case, the intensities at 2125 nm, and 2250 nm might be set to 1 and 3 respectively, and the remaining intensities chosen to satisfy the NAS requirements. There are 2 equations for these 2 unknowns since (i) the sum of X and Y states are set equal, and (ii) the light intensities chosen must produce no difference in response to urea. Together, there are 6 possible cases, and the case giving the largest signal is chosen. This procedure gives the solution shown in Table 7B, with NAS signal for 50 mM glucose equal to 3.4, a gain of 64 percent. For more sources, larger advantages are available, but it becomes unwieldy to check every possibility. In this case, it is useful to use standard techniques from linear programming such as the Simplex method, Karmarkar's method or the ellipsoid method. As will be clear to those skilled in the art, several related techniques can be applied to this problem without departing from the spirit of this invention.

TABLE 7B

Light Intensities for Glucose NAS/Urea By Maximum Powers

| | 2125 nm | 2175 nm | 2250 nm | 2300 nm |
|---|---|---|---|---|
| State X | 1 | 7 | 1 | 0 |
| State Y | 0 | 0 | 0 | 9 |

For example, Table 2 can be multiplied (prescaled) by the available powers of Table 6 to create Table 8. It is possible to apply the original method of NAS calculation to Table 8 and recover the NAS signal shown in Table 9, with a NAS signal at 50 mM glucose equal to 3.35.

TABLE 8

% Attenuation scaled by power available

| | 2125 nm | 2175 nm | 2250 nm | 2300 nm |
|---|---|---|---|---|
| Glucose | 0.92 | 4.02 | −0.11 | −1.67 |
| Urea | 0.0 | 7.21 | 1.89 | 8.71 |

TABLE 9

Light Intensities for Glucose NAS/Urea Prescaled by Power

| | 2125 nm | 2175 nm | 2250 nm | 2300 nm |
|---|---|---|---|---|
| State X | 0.97 | 7 | 1.12 | 0 |
| State Y | 0 | 0 | 0 | 9.09 |

The last step of this procedure is to multiply each component of the prescaled-power NAS by its available power to obtain Table 9. Since it does not involve checking multiple cases, this calculation involves less work, and usually produces a reasonable approximation to the optimal solution in Table 7B. Thus, it may be a suitable choice when computing resources are limited.

These optimizations are also useful when biological variation limits the available power in different ways from measurement to measurement. This application is described in Section 5D 4. Calibrating the Device A. Source and Detector Calibration It is recognized by the inventor that some subsystems of this embodiment will be subject to variations such as temperature related drift that could adversely affect the accuracy and precision of the measurements. Several methods are employed to mitigate these effects.

Briefly, the primary technique is to turn on each light source (one source at a time) and gradually step the controlling DAC through the entire range of settings. At each setting, the output is measured and recorded in a table in the computing device. A curve is then fitted to this data. The curve is used to independently adjust the X and Y state settings for each light source for any given NAS. This method will remove the effects of non-linearity in the light sources and in the associated circuitry. It will also remove the effect of differences in (current to light) transfer function from one light source to another. In a similar fashion, turning on several light sources individually and then in various combinations can measure the non-linearity of the detector and associated circuitry. More specifically, doubling the current into one of the LEDs will yield a light output that is very slightly different from twice the initial light output. The response of the detector will also be slightly nonlinear. By applying known currents to one LED at a time and in groups, stepping the current through the entire range of the system, and storing the results, it is possible to compute the degree of non-linearity of each part the system and apply a suitable correction factor to all other measurements. For additional information, refer to "Light source calibration" and "Detector calibration" in "The Software," below.

These calibration procedures alone, will be sufficient to provide the required accuracy and precision for relative concentrations, but will not yield any information concerning absolute concentration. In order to determine an absolute concentration, one additional step is required. Each source is turned on (one source at a time) and transmitted through a phantom with a known attenuation. Measurements are recorded at two or more input levels. This information can then be employed to transform the previously measured relative data into absolute data. A cuvette containing 1 mm to 2 mm of distilled water has been found to be a suitable phantom for this purpose.

In order to obtain a distribution of path lengths similar to a living biological tissue, more complex phantoms including lipid droplets, polystyrene beads, or animal tissue may also be employed.

B. Biological Calibration

In order to use the apparatus to measure the concentration of an analyte in biological tissue, it is necessary to account for many sources of variability that do not occur in a test tube or cuvette under controlled conditions. Measurements made with our apparatus depend on small differences in light transmission and absorption of light from different light sources. Since biological samples will contain randomly distributed structures, and be of different shapes, sizes and elasticities, the path lengths in the tissue from each source to detector cannot be known in advance with sufficient precision. This variation can result in variation in the signal strength, and can change the apparent transmissions of the different sources from their true values as the light emission and collection systems are moved. In a preferred embodiment of our invention, certain mathematical techniques are used to predict and control variations in signal strength and to avoid corruption of the measurements by uncontrolled changes in path length and probe-to-sample optical coupling.

This type of variation is accounted for by analyzing a calibration experiment. The reasoning behind a calibration experiment may be clarified by an example. During an ideal calibration experiment, there is a single nuisance variable that is systematically varied. For example, a cuvette containing a fixed or zero concentration of the analyte of interest might be systematically rotated in a light beam. The rotation changes the effective path length, and shifts some of light onto, or off the detector as the position changes, because the cuvette acts as a prism. Therefore, in order to accurately measure the analyte concentration as the cuvette rotates, the effect of rotation angle must be accounted for. This requires (i) a way to measure rotation angle and (ii) an equation which describes its effect. In the calibration experiment, any measurement X that is well correlated with the rotation angle, but independent of the analyte concentration, can be a substitute for the rotation angle. A model equation that expresses the relationship between X and the effective path lengths can be used later to mathematically rotate the cuvette back to a zero rotation angle. Thus, the model equation is used during the analyte-measurement phase to remove the effect of nuisance variables. This example is illustrative only and should not be interpreted to restrict the invention.

Figure 8A:
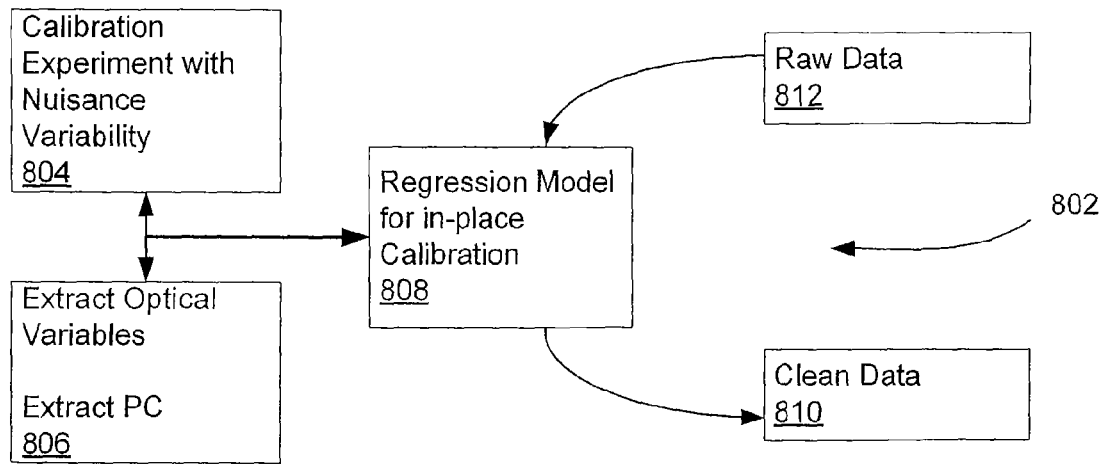
FIG. 8A illustrates the relationship between a calibration experiment and the modules involved in removing nuisance variation from data.

A biological calibration procedure 802 illustrated in FIG. 8A follows the same reasoning, but there are more nuisance variables, and they are identified using techniques from multivariate statistics. FIG. 8A shows that the calibration procedure includes a calibration experiment that exhibits the nuisance variability 804. The data from the calibration experiment is analyzed via an optical variable extraction and compression module 806 that employs principal component (PC) analysis. An in-place calibration module 808 transforms raw data 812 into clean data 810 by subtracting model estimates of nuisance variability obtained from the outputs of modules 804 and 806. These techniques are based on accounting for measurement variability with a small number of parameters. Success depends upon the assumption that the variation that seems to involve many parameters is really due to only a few parameters. For example, as an archer draws a bow the simple motion of his hand causes every point on the bow to move. Similarly, the relationship between 2 or more path lengths, U and V may reflect the common influence of another factor. For example pressing on the middle of a sample may cause it to bulge simultaneously at both ends. Such common factors lead to a linear or curvilinear relationship between 2 or more path lengths when they are plotted with U on the abscissa and V on the ordinate of a graph in replications of the experiment. These relationships are not limited to those due to pressure on the sample, but may also include probe-to-skin pressure distribution, mean source-to-detector path length, skin moisture, tissue temperature, pH, osmolarity, hemoglobin oxygenation, tissue vascularization and tissue fat content.

To make use of this inherent simplicity, principal component analysis and regression analysis are performed on data from a calibration experiment. The principal component analysis identifies the nuisance variables in their simplest form, and the regression analysis computes the relationships between the nuisance variables and optical measurements that are independent of analyte concentration. In a preferred embodiment of our invention, the optical measurements provide estimates of the unique set of source-to-detector path lengths and other nuisance variable values which result each time the sample is placed in the apparatus.

Principal component analysis is a technique that can eliminate redundancy in a multivariate set of measurements by finding the principal directions of variation. Thus it reduces the dimensionality of the data without much loss of information, much as a fingerprint summarizes important information about a finger while discarding three-dimensional information. As is well known to those skilled in the art, extracting the eigenvalues and eigenvectors from the covariance matrix of the multivariate data performs principal component analysis. Subsequently, each data point may be reassembled as a linear sum of the eigenvectors, or principal components. That is, the principal component analysis allows a compressed version of the data set to be used, so that without much loss of information, each multivariate data point may be expressed as a combination: $z_r = w_1 P_1 + w_2 P_2 + \ldots + w_m P_m$ where $P_j, j=1, m$ are the principal component vectors and m is much less than the original number of components in the vector $z_r$. The data points from the calibration experiment summarize the nuisance variability, but do not contain specific information about the causes of the variability. To make use of this summary it is necessary to create a model equation that relates nuisance variability to optical measurements that are available without moving the sample, and that are not confounded with the information used to determine analyte concentration.

Figure 8B:
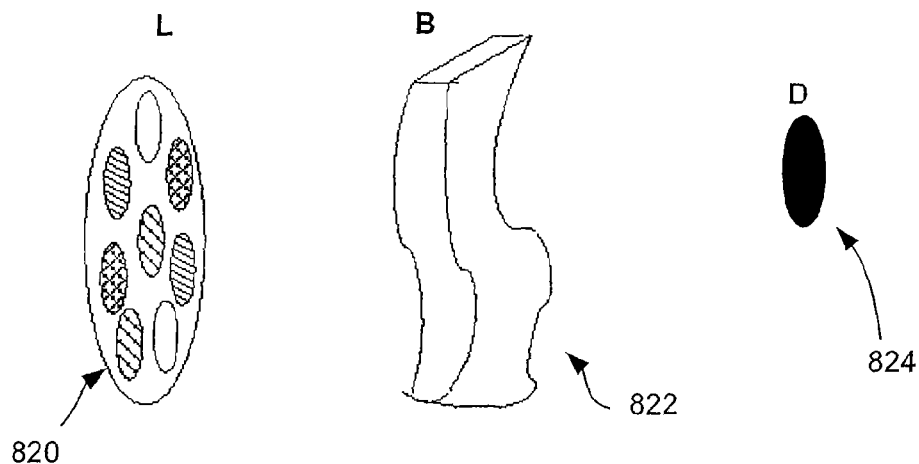
FIG. 8B illustrates the method of light source duplication for biological calibration.

In a preferred embodiment of our invention, light sources emitting the same wavelengths are duplicated at two or more spatial locations within the light generation module as shown in FIG. 8B. FIG. 8B shows the emitting bundle of a light generating module (L) 820, with sources of equal wavelength indicated by hatching quality, an irregularly shaped biological sample (B) 822 and a detector (D) 824. Nothing in this drawing shall be taken to restrict the invention to a specific number of sources or a particular optical design, since it is for illustrative purposes only. The ratio, or difference between light transmissions for the duplicated sources only contain information due to the sample placement and shape, (or other nuisance variables) since differences in transmission between sources of equal wavelength cannot be due to wavelength. To calculate such an optical variable, for example, the light transmitted through the sample from source p is measured as $t_p$ while the transmitted light intensity from another source q, of equal wavelength is measured as $t_q$, then the variable $$x_j = \frac{t_p}{t_q},$$

j=1,l is an optical variable. These combinations of equivalent sources may be chosen arbitrarily, though once chosen, they remain fixed. The variables $X_j$ are measured during the calibration experiment and for each sample placement during the subsequent analyte-measurement phase. The quantities $x_j$ are the substitute model variables (X of the cuvette example) that are inserted into the calibration model equation to estimate nuisance variation. In one embodiment, the ith equation for each principal component weight is: $w_i = A_0 + A_{i1}x_1 + A_{i2}x_3 + A_{i3}x_3 + \ldots + A_{ik}x_k$ where $A_{ij}$, i=1,m, j=1,l is a numerical coefficient and $w_i$ is the weight to be inserted into the principal component version of each data point to calculate the nuisance variation.

Finally, the analyte-measurement-phase data are cleansed of nuisance variation by subtracting from each data point the nuisance variation estimate: $u_r = w_1 P_1 + w_2 P_2 + \ldots + w_m P_m$ where $w_i$, i=1,m are calculated as described. These are linear equations but it will be appreciated by one skilled in the art that the underlying constraints and equations may be polynomials or trigonometric basis functions without departing from the spirit of the invention. In addition, more general multivariate techniques such as partial least squares may also be use to accomplish the same purpose, as is known to those skilled in the art.

C. Source Temperature Calibration

The inventors recognize that both the intensity and distribution of wavelengths of the light sources are a function of the temperature of the source. Since the principle of operation of the device is to control light outputs for different sources at a predetermined level, it may contain modules which measure the temperature, control the temperature and/or stabilize the light output by controlling input drive current as the temperature varies. A practical device should reach operating temperature quickly, and accurately stabilize light output from all the sources simultaneously while the measurement is performed. Light output stabilization can be achieved in two ways, which are (i) control of temperature and (ii) changes in input current which compensate for changes in temperature. Precision requirements for temperature measurement and control are less demanding than those for analyte measurement, because light output is dominated by the current input to the source, rather than temperature. For example if 17 bits of accuracy in the light output are required for analyte measurement, then 12 to 13 bits of accuracy might be required for temperature measurement and control. The lesser influence of temperature also means that small changes in input current may be sufficient to compensate for anticipated changes in temperature.

In a preferred embodiment of our invention, the junction temperatures of the light sources are measured continuously, temperature control schemes based on a heating model are used to rapidly bring temperatures within a calibrated region, and light output is held constant during the measurement by adjusting current inputs. The current inputs necessary to stabilize the light output are calculated using a calibration function specific to each light source. This calibration function gives light output as a joint function of current input and temperature. If temperature could be held perfectly fixed, the calibration experiment could consist of one measurement; while if temperature is not controlled and the effect of temperature on light is non-linear, the calibration experiment must consist of a wide range of measurements. In view of this tradeoff, those skilled in the art will recognize that different combinations of temperature control and calibration may be employed without departing from the spirit of this invention.

Temperature monitoring can be achieved by several means, including thermistors and thermocouples. However in one embodiment of our invention, temperature measurement at the semiconductor junction of the light source is performed using the forward voltage drop of the source. This approach is preferred because temperature gradients within the light source may limit the accuracy of measurements made using thermocouples or thermistors. The forward voltage drop across a diode junction is a function of the diode current and of the junction temperature. The equation describing this relationship is the well known diode equation:

$$I_d = I_s(e^{qV/NkT} - 1)$$

where:
$I_d$=Diode current
$I_s$=Reverse bias current (typically $1 \times 10^{-12}$ ampere)
e=Euler's constant (2.7182 . . . )
q=Electron charge ($1.6 \times 10^{-19}$ coulomb)
V=Voltage across the diode
N=Emission coefficient (typically between 1 and 2)
k=Boltzmann's constant ($1.38 \times 10^{-23}$ m$^2$ kgs$^{-2}$K$^{-1}$)
T=Junction temperature (in degrees Kelvin)

Therefore, when the current is switched between two values (as is the case in the device being described), the difference in the voltage drop $\Delta V$ at the two currents is nearly proportional to $(kT/q)\ln(I_2/I_1)$. In prior art this formula is known to be accurate over a wide range of temperatures for silicon. Small departures from linearity that may exist for other materials (such as GaSb) can be dealt with by calibration.

Solving for temperature and absorbing the proportionality constant yields:
T=q $\Delta V/k \ln(I_2/I_1)$ where:
$I_1$=The lower of the two currents
$I_2$=The higher of the two currents
$\Delta V$=the difference in voltage across the diode at the two currents.

The sensitivity of the resulting temperature measurement according to this formula is indicated in the table below. With this method it is practical to measure the junction temperature of each diode with a precision on the order of a tenth of a degree. Averaging several measurements may increase the precision further by reducing noise.

TABLE 10

Temperature Measurement Slope

| Ratio $I_2/I_1$ | µV per degree K. |
|---|---|
| 2 | 60 |
| 5 | 139 |
| 10 | 200 |

In order to make use of the temperature measurements for light stabilization it is necessary to construct a function relating light output to (i) current input and (ii) temperature for each of the light sources. The properties of this function depend on the semiconductor material in the light source and the band pass characteristics of any optical filter used to restrict the set of output wavelengths. Within a sufficiently small range of light output and temperature (calibration region), this function could be approximated by a linear relationship: $L=(A_0 + A_1 T)I_d$ where L is light output, $I_d$ is the current input to the source, T is junction temperature and $A_0$ and $A_1$ are constants to be estimated. However it may be understood by those skilled in the art that non-linear approximating functions such as polynomials could also be used to extend the accurate calibration region without departing from the spirit of this invention. Once the function has been constructed, the temperature of each source can be continuously monitored and used to adjust the input current to maintain a constant output intensity L after solving the equation for $I_d$.

In an alternative embodiment of the invention, temperature-related drift can be measured by diverting a portion of the light from each source before it passes through the sample, and using a measurement of the diverted light to stabilize the light output. This diversion might be done with a partially reflective mirror. A suitable analog or digital feedback scheme could then stabilize light output without the need for calibration.

In order to get accurate results in the light stabilization scheme it may be necessary to also stabilize the temperature so that it remains in a suitable calibration (operating) region. When the sources have large thermal inertias, thermal inertia (heat capacity) can prolong the times required to reach the operating temperature, or to cool to operating temperature after a period of heating. Therefore, a thermoelectric cooler may be added to the apparatus in order to reduce the time necessary to reach thermal equilibrium, or to return the heat reservoirs to a temperature that is at or below the ambient temperature after a period of heating. A second way to stabilize the temperature within the operating regions is to turn the sources on and off for controlled periods, calculated from a heating model. Because the light sources may be in thermal contact with one or more heat reservoirs or heatsinks, the temperature trajectory when the source is turned on depends on how long it has been on previously. For example, the rate of temperature rise after turn-on will be faster when the heat sink is hot than when the heat sink is cold. When the heat sink is large, and this change in behavior can last minutes or hours. For this reason, effective temperature control will be aided by a heating model that summarizes information about the heat reservoirs that are in thermal contact with the semiconductor junction. The heating model can be used to exactly calculate the amount of on-time or off-time necessary to steer the temperature to a desired value within the calibration range. For example, the heating model might be summarized by FIG. 8C, which shows two connected heat reservoirs; the first reservoir 830 with capacity $C_l$ and second reservoir 832 with capacity $C_s$ connected with thermal conductivity d, with the first reservoir receiving a heat input of power $s_0$ and both reservoirs insulated from the environment.

Figure 8C:
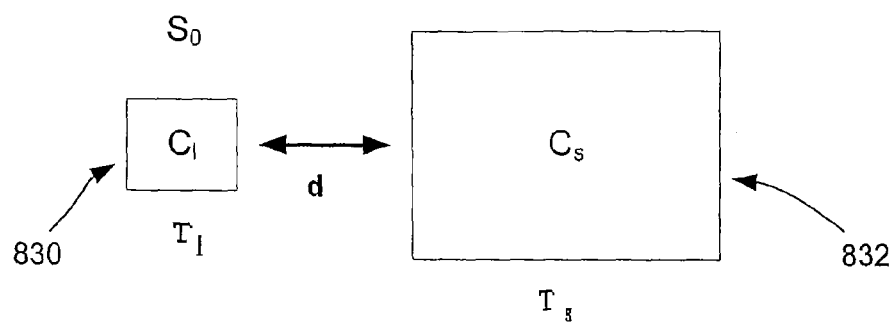
FIG. 8C illustrates one embodiment of a prediction module for the internal temperatures of the light sources.

In FIG. 8C, the reservoir with subscript 1 corresponds to the light source, and the reservoir with subscript s corresponds to a heat sink. As is well known, the equations for temperatures $T_l$ and $T_s$ in such a system are given by the equations $C_l \partial T_l = s_0 + d(T_s - T_l)$ and $C_s \partial T_s = -d(T_s - T_l)$, where the $\partial$ denotes the rate of change in time. Nothing in the drawing or description shall be taken to restrict the scope of the invention to two heat reservoirs, or to reservoirs insulated from the environment. This is just one embodiment of the invention, and the drawing is for illustrative purposes only. The solution to this system is $$T_l = \frac{1}{C_l}\left(U_0 + s_0 t - \frac{U_0 P_0}{D}(e^{Dt} - 1) - \frac{P_0 s_0}{D^2}(e^{Dt} - 1 - Dt) - V_0 e^{Dt}\right)$$

where t is time, $D = -d(1 + C_s/C_l)/C_s$, $P_0 = d/C_l$, $U_0 = C_l T_l(0) + C_s T_s(0)$ and $V_0 = C_s T_s(0)$. The notation T(0) denotes the temperature at time 0. This solution allows the prediction of future temperatures in a system of 2 heat reservoirs with known initial temperatures and may also be inverted using well known techniques such as Newton's method to determine how long to turn the sources on or off in order to achieve a desired temperature. The heat sink temperature $T_s$, which is not monitored, may be determined from observations of the rate of change of the light source temperature $T_l$ using the equations. Direct measurements of the parameters d, $C_l$ and $C_s$ are not required. These parameters may be found by performing an experiment in which the light sources are turned on and off at controlled current levels and the heating and cooling rates are observed. These observations can be used to estimate the parameters in the model using well-known techniques for least squares curve fitting.

While temperatures are measured continuously in the embodiment described, other embodiments might make use of the heating models to perform the functions disclosed using intermittent measurements of temperature, and intermittent or staggered sending of commands to the light module while remaining within the scope of this invention. This approach may be useful when data acquisition rates for temperature measurement, computation speed, or command transmission rates to the light source controllers are limited. When there are many sources, delays as small as 50-100 ms per source due to data acquisition, computing and transmission of commands to the light module can lead to cumulative delays of 1-2 seconds between a control command sent to the first source and the last one. A suitable schedule calculated from the heating model can assure the light sources still reach the operating temperatures simultaneously, even when command and measurement delays reach several seconds.

5. Software

In order to create a working prototype of an embodiment of this invention, a number of computational tasks must be controlled by software. This section describes the tasks, which need to be accomplished and the design of the software modules involved.

There are 2 types of software involved. One type is device dependent, and should be reproducible by one skilled in the art, who has access to the manufacturer's specifications for a particular device. The necessary functions (include but are not limited to communication with commercially available analog to digital (ADC) and digital to analog (DAC) converters, embedded microprocessors, or charge integration amplifiers. For example, such software must send appropriate timing signals to the hardware, and send and fetch the required data from the hardware registers provided according to protocols specified in a published set of instructions.

Figure 7:
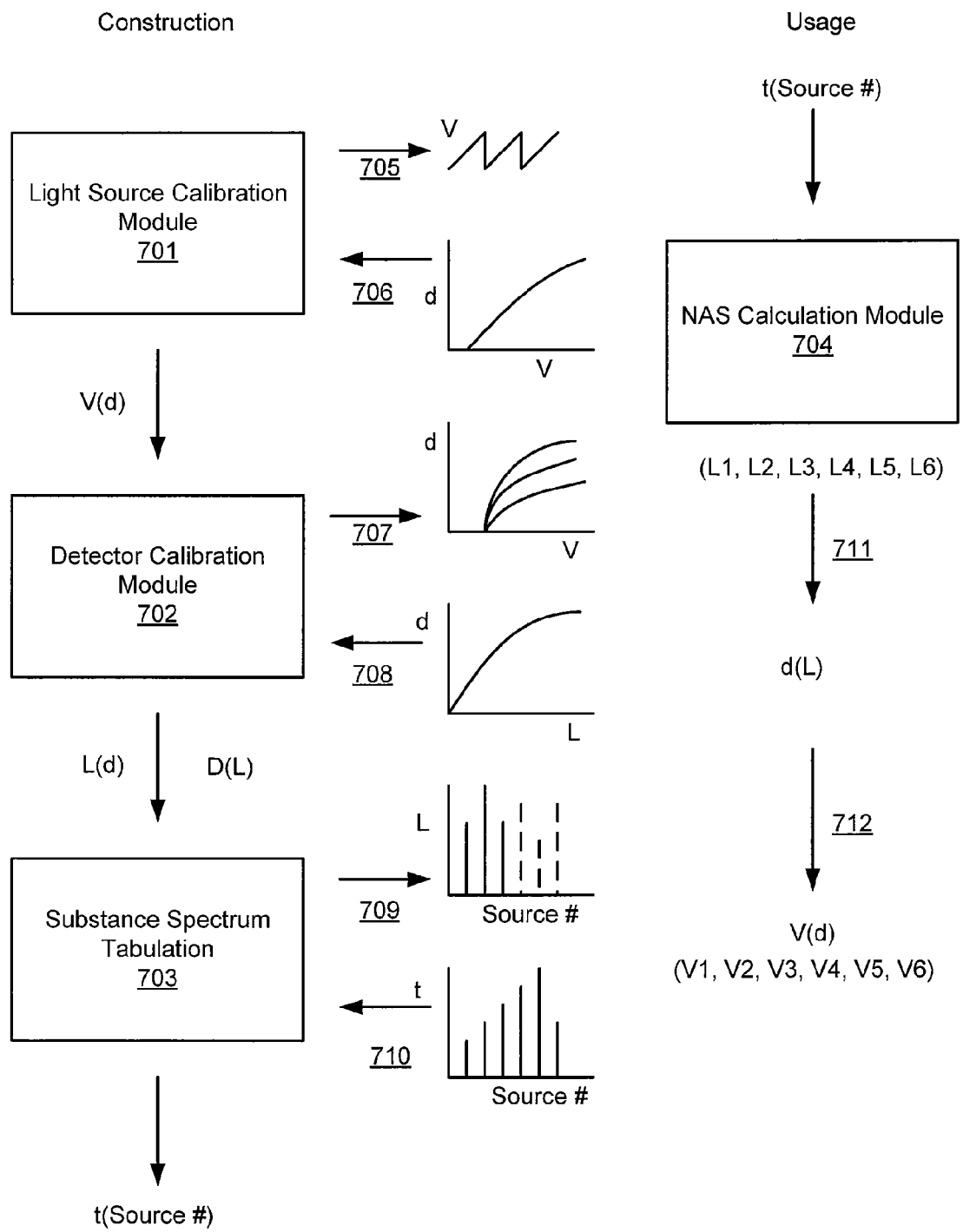
FIG. 7 illustrates the relationships of the various software elements to an embodiment of the invention.

A second type of software implements the theoretical methods and converts them to a form useable by the hardware. This software will be described in more detail. Refer to FIG. 7. It consists of software modules for light source calibration 701, for detector calibration 702, for substance spectrum tabulation 703 and for NAS calculation 704. In addition to implementing theoretical methods, these modules must sometimes accomplish tasks in an indirect manner because of non-ideal properties of the hardware such as non-linearity and drift. In FIG. 7, V denotes DAC voltage, d denotes detector response, and L denotes light.

Other necessary software functions which constitute design choices in different embodiments of the invention, such as methods to choose a suitable set of light source wavelengths, methods to check the correct functioning of the equipment, and methods to enforce timing patterns on the signal are also described.

A. Light Source Calibration

In the light source calibration, light output is controlled using an input voltage generated by a DAC. It is necessary to accurately store the relationship between the DAC voltage and the detector response. In the present software embodiment this is achieved by instructing the DAC to generate a linear voltage ramp 705 between zero and a maximum value that is repeated in time at a low frequency between 1-100 Hz. Other embodiments may use other patterns of calibration input. Multiple points (5-50) on the curve are tabulated, and a polynomial curve 706 is fitted to the relationship between the DAC voltage and the detector response using the method of least squares. The degree of the fitted curve is between 2 and 10 and is adjusted according to the non-linearity and noise level in the data. In other embodiments, other types of curve such as trigonometric functions or splines might be used. In order to make practical use of this information it is necessary to create an inverse curve. That is, the useful stored form of calibration must begin with a desired light level and obtain the corresponding DAC voltage. To generate an accurate inverse curve, the polynomial is re-sampled at a large number (50-500) points and cubic functions are fitted between each set of 4 successor points. The software contains the means to recognize fitted functions that are inappropriate, such as curves that contain local maxima or minima. In addition, the software uses a matrix condition number to recognize degenerate situations when 3 successor points fit on a line, or 4 on a quadratic, and takes action to replace the (possibly inaccurate) cubic function with the lower order curve. Units are appropriately scaled within the software module so that the light output is measured in ADC counts and the input DAC voltage corresponds to light source input current. The inverse lookup procedure first locates the successor points, which bracket the desired detector response, and then obtains the necessary source current from the fitted local inverse curve.

B. Detector Calibration

While the light source calibration establishes a relationship between DAC voltage and the detector response, it is necessary to know how the relative detector response corresponds to a physical light input. For example, a doubling of the light input may not result in a doubling of the detector response. In the detector calibration procedure it is assumed that the same function of detector response to input light power 708 applies at different wavelengths.

The detector calibration module instructs the DAC circuits to create a series of voltage ramps in which different numbers of light sources are turned on at the same time. In one embodiment, 3 sources, A, B, C are each driven with a voltage ramp chosen so the maximum intensity for each light source is the same value L. The voltages that give light output L can be established using the result of the light source calibration module. They are then turned on 707 so that the first source A emits a ramp with maximum intensity, L, then A and B together emit a ramp with maximum intensity 2L, and then A, B and C together emit a ramp with maximum intensity 3L. Next, another source D is set to a constant value of 3L. This is usually possible because some sources have much more available power than others. Thus, the combination D+A will produce a ramp with floor 3L and maximum 3L+L, the combination D+A+B will produce a ramp with floor 3L and maximum 3L+2L, and the combination D+A+B+C will produce a ramp with floor 3L and maximum 3L+3L. In this manner it is possible to produce input light intensities 0, L, 2L, 3L, 4L, 5L and 6L and fit a detector response curve of light intensity versus detector response 708 which may be inverted in a manner similar to the one described for the light source calibration. If there is a non-zero baseline, it can be added. When detector non-linearities are not pronounced, a small number (such as the seven listed) of points on the curve may suffice. The degree of the detector polynomial curve in present embodiments is chosen between 2 and 4.

It is convenient to use ramp inputs because this allows common algorithms to be applied in light source and detector calibration modules. In other embodiments, however, the calibration described above could be performed without using voltage ramps, since only single DAC voltage points are used.

If some additional conditions are true, additional points on the curve may be obtained from the same data. If it is assumed that light ramps with the same maxima are equal throughout the range of the ramp i.e., light ramps follow identical curves from each source from 0 through the maximum; (uniformity assumption) additional points may be calculated as follows.

As an example, let $I_{32}$ denote the current(s) such that the A+B+C combination ramp attains the maximum intensity of the A+B ramp 2L. Then $(A+B)(I_{32})=2/3*2L=4/3L$, because turning off source C at level $I_{32}$ in the A+B+C ramp removes ⅓ of the light under the uniformity assumption. While the uniformity assumption is only approximately valid, the detector calibration software computes these points and other similarly determined data points. This is done as a check on the uniformity properties of the light ramps, and is a useful check on any errors that may be introduced by transient sources of noise and improper functioning of the equipment.

The detector calibration is used when it is necessary to generate a certain level of physical light from a source or set of sources. Typically the NAS calculation requests light levels from each source, the inverse detector curve translates the requested light levels to detector responses 711 and the detector responses are inserted into the inverse light source calibrations to obtain the necessary DAC voltages 712.

C. Substance Spectrum Tabulation

In order to compute a NAS it is necessary to acquire baseline data on the spectra of the substances involved. As the light sources in the apparatus may be separated in space, it is difficult to obtain accurate estimates of what the observed attenuation for each source will be from published data alone. Because the theoretical calculations are based on this data, it is desirable to obtain a highly accurate tabulation of the spectra of interest within the apparatus of the present invention. One apparently simple way to perform the substance spectrum tabulation would be to turn the sources on, one at a time, and compare the attenuation in the presence of water with the attenuation when the substance of interest is present.

However because of power limitations, some light sources may appear to be much weaker or stronger than others. This amplifies the ill effects of detector non-linearity particularly if there is any wavelength-dependent non-linearity. The detector calibration is likely to be invalid for levels that are much less than the original spacing between calibration points L (refer to the previous section), so that the standard detector calibration is not a sufficient solution when the range of source magnitudes is large. In addition, light sources may exhibit different drifts in light output depending on the input current and the switching schemes employed. Therefore it may be undesirable to drive the sources at very different input current levels.

The substance spectrum tabulation module controls source outputs and acquires data on relative attenuation of each light source in a way that is designed to mitigate the problems stated above. During spectrum acquisition, several different turn-on modes are used. In each mode a subset of the sources is switched on in state X and off in state Y, while the remaining sources are off in state X and on in state Y. If there are N sources this is done for N modes.

For the module example in one embodiment there might be 6 sources, with the substance tabulation requesting light levels A, B, C, D, E, F based on a water calibration. In this case, there would be 6 modes such as: mode 1: state X, A+B+C=1.0, D=E=F=0; state Y, A=B=C=0, D+E+F=1.0; or mode 2: state X, A+B+D=1.0, C=E=F=0; state Y A=B=D=0 and so on up to mode 6. Modes must be chosen to give independent information. In the presence of the substance, attenuations differ from those when only water is present, so that instead of observing a net output of A+B+C=1.0 in mode 1: state X, a net output $At_a+Bt_b+Ct_c=1+x_1$, would be seen and in state Y, a net output of $Dt_d+Et_e+Ft_f=1+y_1$ would be observed instead of 1.0, where the $t_i$ represents transmission in the presence of substance i relative to transmission in the presence of water. Similarly, the presence of the substance changes the observed output for each mode. The light levels A, B, C, D, E, F are coefficients in 6 linear equations, and the observed outputs appear on the right hand sides of the equations (denoted by $1+x_i$ and $1+y_i$) in the equations above. Finally the resulting linear equations are solved to determine the attenuations/ transmissions ($t_a$, $t_b$, $t_c$, $t_d$, $t_e$, $t_f$) of each of the 6 sources in each light combination 710. In this arrangement, the levels of input light remain similar, and all the light sources are operated continuously (although at slightly different levels in each subset) throughout the substance tabulation procedure. These acquisition modes are automatically generated by the software based on information from the source and detector calibration.

In one particularly useful scheme, a set of suitable fixed levels A1, A2, B1, B2, C1, C2, D1, D2, E1, E2, F1, F2; might be selected and the levels might be reversed one by one to create each of the 6 modes. For example, if the list above denotes a mode in which source A is at level A1 in the X state and A2 in the Y state, then the second mode might be A2, A1, B1, B2, C1, C2, D1, D2, E1, E2, F1, F2. This is useful because duty cycles and levels remain constant through all modes, thus minimizing temperature drift.

To deal with any calibration drift (source or detector) between the original calibration and the time of the substance calibration, the substance spectrum is acquired immediately after a water baseline. The water baseline is used to calculate a set of short-term correction coefficients a, b, c, d, e, f which reset A→A'=aA, B→B'=bB, etc. so that the current water baseline gives a result which is exactly consistent with the calibrations. Exact consistency is achieved by requiring that the new coefficients A', B', C', D', E', F' exactly match the observed right hand sides (denoted by $1+x_i$ and $1+y_i$) for the water baseline.

D. NAS Calculation

The user interface to the software environment of the current embodiment is designed such that each calibration procedure has a summary file as output. These summary files, that contain the results of each calibration and tabulation, must be read by the program before the NAS calculation module is activated. Once this is complete, the NAS calculation module calculates an NAS for each substance relative to the others at the request of the user. It will also produce an estimate of the signal size expected at the concentration used for spectrum tabulation.

The NAS calculation module combines information about the substance spectra, and produces an NAS using the mathematical procedures described in the theory of operation. This NAS, which is expressed in (arbitrary) physical light units L, is converted into a set of state X and state Y DAC voltages 712 by performing the lookup and interpolation procedures 711 described in the previous sections. Because the available power from different sources can vary widely, it can happen that the NAS calculation initially requests a set of light levels that require more power than some of the sources can produce. The methods described in Section 3 can be used to obtain the maximum possible signal for the available powers when this occurs. Available power is also modified by the properties of each biological sample. These variations can be compensated as follows.

In a biological measurement, the effective power available from each source will be modified by the optical coupling and path length that occurs each time the probe is placed during calibration and analyte measurement phases, with each source affected differently. The data from suitable calibration experiments allows the NAS signal to be maximized for each placement and may reduce variation from sample to sample. This is useful because it is known in prior art that variations in probe-to-skin coupling can lead to large variations in the signal received from light passing through tissue.

As will be clear to those skilled in the art such calibration experiments must be designed to correctly attribute variation due to path length and coupling during calibration and analyte-measurement phases, in order to avoid erroneous results. Specifically, controls must be added to this calibration experiment so that variation is independent of other factors, such as temperature or changes in the concentration of the analytes. It must also be established that variation is correctly attributed during the analyte measurement phase.

If the calibration experiment only summarizes coupling and path length changes from sample to sample, then the procedure for removing nuisance variation described in section 4 B effectively adjusts each source-to-detector path length so that it is the same for each sample. Thus, the calibration equations can be inverted to estimate the powers $\tilde{W}_a$ that would be available if the sources were turned up to maximum power through these coupling conditions and path lengths. The available power estimate $\tilde{W}_a$ can be used in place of the maximum power constraint $W_r$ (example in Table 6) in the procedure that maximizes the NAS, given in Section 2. This procedure may produce a viable signal even if a small number of the sources are coupled poorly or not at all.

The equation used to estimate the available power is: $\tilde{W}_a = W_r + AW_r$ where $W_r$ are the known raw powers, A=diag$(w_1 P_1 + w_2 P_2 + \ldots + w_m P_m)$ is a diagonal matrix formed from the entries of the vector sum $w_1 P_1 + w_2 P_2 + \ldots + w_m P_m$, where $w_i$ are the weights calculated from the calibration model, and $P_i$, i=1,m are the principal component vectors from the calibration experiment. The sign in this formula is positive in contrast to the nuisance variation cleaning procedure because the equation for $\tilde{W}_a$ gives a result proportional to the available transmitted power which would be observed with the given source-to-detector path lengths, while the variation cleaning formula gives the signal which would have been observed with path lengths equalized across samples. These relationships are approximately inverted by a change of sign.

An alternative procedure to estimate maximum powers is to turn the sources on at their maximum powers, one by one. However, this may produce erroneous results when nuisance variables other than path length or coupling contribute significantly to the variation during the analyte measurement phase.

When the nuisance variation is dominated by changes in mean path length, optical variables which are ratios of transmissions between sources of equal wavelength may not be suitable, since the ratios are insensitive to the sizes of the light intensities in the numerator and denominator. In this case, supplementary measures of mean path length such as a water NAS, or attenuation of an independent light source should be used in addition to the optical ratio variables. While these supplementary measurements may also be confounded with individual source path length variations, such mean path length measurements require less measurement precision because they are based on attenuation through highly absorbing substances.

E. Source Selection

The method disclosed here is unlike others because the mathematical choice of the wavelengths in a particular NAS becomes a specific choice of light source hardware elements such as LEDs. A software simulation is employed to aid in the choice of source wavelengths that would be most effective in creating the NAS for glucose, or other substances.

To create these simulations, published data on the spectra of substances of interest, as well as data on commercially available light sources and optical filters is tabulated. At least 2 methods may be used to choose suitable wavelengths. In one method, more suitable for large numbers (>6) of sources, the effect of bandwidth and central wavelength are explored, assuming equally spaced increments of the central wavelength. In another type of simulation, more suitable for smaller numbers of sources, smaller subsets (2-6 sources) from a longer list of commercially available filters can be exhaustively examined to determine optimal choices. In each case, the software computes a simulated NAS by the methods described above, substituting published data for real observations at each stage and tabulating the size of the signal that would result in a particular subset. The best choice of a NAS is the one generating the largest signal.

F. Data Synchronization

Under ideal conditions, all differences between the X and Y signals will be either zero (when the analyte of interest is not present) or positive (when it is present). Negative differences should not occur. The inventors recognize that in some circumstances (such as the presence of a totally unanticipated interfering analyte, the failure of one light source, inaccurate calibration, and other possibilities) negative differences may occur. Any significant negative signal should be interpreted as being invalid data with respect to the analyte of interest.

Therefore, in controlling the DAC hardware it is necessary to choose some method to discriminate between the X and Y states within the acquired data. This is because the observation of a positive difference X-Y and a negative difference X-Y have different meanings. The method used to accomplish this is a design choice that is not entirely hardware specific. While this task is not performed by a single module, it is a method-specific task that must be built into the hardware-specific interface. It will be appreciated by one skilled in the art that there are several means to accomplish this task. One possibility is to record (on the same time axis as the output data) a timing signal generated by the hardware that may be identical with the DAC output, which is non-zero in the X (or Y) state. A second possibility is to create a repeating sequence in which the X and Y state pulses may be identified by their positions in the sequence. For example, one embodiment uses a repeating 37-point sequence in which the first 2 points are set to zero. In each such sequence, the X state immediately follows a pair of zeros and the X and Y states subsequently alternate, 35 times with 18 pulses for the X state and 17 pulses for the Y state.

6. Applications

Embodiments of the present invention may be useful whenever it is desired to measure the concentration of a target analyte that has a unique set of absorption coefficients in the near IR, far IR, visible or UV spectrum. Potential applications beyond glucose monitoring include many other situations in which it is useful to measure the chemistry of living tissue non-invasively. These include (but are not limited to) monitoring levels of therapeutic drugs such as antibiotics in the blood or extracellular fluid, clinical assessment of lesions in or on the body on the skin, arterial wall, in the stomach or intestine, or other areas accessible to optical probes. It may be used to assess blood levels of urea, $CO_2$ or carbon monoxide in patients with compromised organ function, and may be especially useful for rapid screening or in unconscious patients.

Laboratory applications include the testing of blood samples, plasma, urine or other body fluids and tissue samples outside the body. Similarly, the invention may be used for monitoring the chemical composition of industrial production processes, such as those involved in food or beverage production, and monitoring of chemical reactors such as those used in petroleum production or pharmaceutical production. It may also be used in quality control for production of other materials (such as plastics) based on organic synthesis.

Agricultural applications may include disease diagnosis, soil analysis, water analysis, quality control for grapes or coffee beans, and assessment of fruit ripeness or sugar content in oranges, strawberries, apples or other fruit.

Finally, the invention may have applications in detection of illegal or dangerous substances, crime scene analysis, remote imaging of chemical composition, and intoxication and sobriety testing.

While the description above refers to particular embodiments of the present embodiments of the invention, it will be understood that many modifications may be made without departing from the spirit thereof. The accompanying claims are intended to cover such modifications as would fall within the true scope and spirit of the present embodiments of the invention. The presently disclosed embodiments are therefore to be considered in all respects illustrative and not restrictive, the scope of the embodiments of the invention being indicated by the claims in a non-provisional patent application, rather than the foregoing description, and all changes which come within the meaning and range of equivalency of such claims are therefore intended to be embraced therein.

What is claimed is:

1. An apparatus for measuring a concentration of a target analyte in a sample containing at least one alternate analyte, the apparatus comprising:
   a light generation module comprising at least three light sources simultaneously generating a plurality of light wavelength bands, each light band of a narrow wavelength, the at least three light sources together comprising a non-monochromatic source;
   the light generation module switching each of the plurality of light wavelength bands between two or more predetermined intensities;
   a light combination module comprising a plurality of light-directing optical elements for combining the plurality of light bands into a narrow beam;
   a focusing module comprising at least one of a module for directing: (1) the narrow beam onto the sample and (2) the light collected from the sample onto a detector;
   a detector for receiving light having passed through or reflected from the sample;
   a measurement module for measuring a sum of received intensities of a set of the light bands in the narrow beam which have passed through or reflected from the sample; and
   a determination module comprising a processor and circuitry for choosing the predetermined intensities of each of the plurality of light bands emitted by the light generation module so that a sum of the received intensities of the light bands which have passed through or reflected from the sample is a function of the concentration of the target analyte.

2. The apparatus of claim 1, wherein the light generation module further comprises at least three light sources, each of the light sources configured to generate one or more of the plurality of light bands.

3. The apparatus of claim 2, wherein the light generation module is configured to control an average or instantaneous intensity of the plurality of the light bands.

4. The apparatus of claim 3, wherein the light generation module is configured to control the intensity of each of the plurality of the light bands.

5. The apparatus of claim 4, wherein the determination module determines a predetermined intensity of each of the plurality of light bands emitted by the light generation module using mathematical techniques from the theory of orthogonal vectors so that a difference between a first sum of the received intensities of a first set of light bands in the narrow beam and a second sum of the received intensities of a second set of light bands in the narrow beam which has passed through or reflected from the sample is proportional to the concentration of the target analyte and insensitive to the concentration of at least one alternate analyte.

6. The apparatus of claim 5, wherein the mathematical technique used by the determination module calculates the net analyte signal of Lorber.

7. The apparatus of claim 5, wherein the said difference of a first sum of received intensities and a second sum of received intensities is corrected for a plurality of nuisance variables including at least one of: (1) sample temperature; (2) instrument drift due to light source temperatures or aging of components (3) sample pH; (4) sample water content; (5)

sample hemoglobin oxygenation; (6) sample's tissue optical properties; and (7) parameters of the optical coupling between the focusing module and the sample.

8. The apparatus of claim 7, wherein the determination module chooses the predetermined intensities of the generated light bands for maximizing the amplitude of said difference between the first and second sums of the received intensities of the sets of the plurality of light bands using a linear programming technique.

9. The apparatus of claim 8, wherein the linear programming technique is a simplex technique.

10. The apparatus of claim 2, wherein the plurality of light bands further comprises at least two sets of light bands such that a difference between the sums of the received intensities of said sets of light bands in the narrow beam having passed through or reflected from the sample is a function of the concentration of the target analyte in the sample and is independent of the concentrations of the alternate analytes in the sample.

11. The apparatus of claim 2, wherein the light generation module switches each of the plurality of light sources between the two predetermined intensities in a synchronous manner such that at any given time each of the plurality of light sources are at one of the predetermined intensity levels.

12. The apparatus of claim 1, wherein the determination module further comprises means to determine the concentration of the target analyte in a composition of analytes wherein for each said at least one alternate analyte which varies in concentration, the target analyte absorbs in a manner different than said at least one alternate analyte for at least one of the plurality of light bands.

13. The apparatus of claim 12, wherein the composition is at least one of: (1) a living organism; (2) a material of biologic origin; and (3) an agricultural product.

14. The apparatus of claim 1, wherein the target analyte is glucose and wherein the sample is a part of a human body.

15. The apparatus of claim 1, wherein each of the plurality of light sources are at least one of a: (1) a light emitting diode (LED); (2) a laser generator; (3) a superluminescent diode; and (4) a thin film infrared generator.

16. The apparatus of claim 1, wherein each of the plurality of light sources further includes an optical bandpass filter.

17. The apparatus of claim 1, wherein the light combination module is a fiber optic assembly.

18. The apparatus of claim 1, wherein the focusing module is implemented by a non-imaging concentrator.

19. The apparatus of claim 1, wherein the measurement module further comprises means to identify and measure the electrical signal using the switching pattern used by the light generation module to switch each of the plurality of light sources between two or more predetermined intensities.

20. The apparatus of claim 2, wherein the light generation module is further adapted to monitor internal temperature of at least one of the plurality of light sources and to calibrate output of the plurality of light sources according to their internal temperatures.

21. An apparatus for measuring a concentration of a target analyte in a sample containing at least one alternate analyte, the apparatus comprising:
  a light generation module comprising light sources for generating a plurality of light wavelength bands each band of a narrow wavelength;
  a light combination module comprising a plurality of light-directing optical elements for combining the plurality of light bands into a narrow beam;
  a focusing module comprising at least one of a module for directing: (1) the narrow beam onto the sample and (2) the light collected from the sample onto a detector;
  a detector for receiving light having passed through or reflected from the sample;
  a measurement module to measure a sum of received intensities of a set of the light bands which have passed through or reflected from the sample;
  a processor for choosing a generated intensity of each of the plurality of light bands emitted by the light generation module so that the received intensity of the combined light transmitted through or reflected from the sample is a function of the concentration of the target analyte;
  wherein the light generation module further comprises light sources, each generating one or more of the plurality of light bands;
  wherein one or more of the plurality of light sources generating a single light band are duplicated at different spatial locations within the light generation module; and
  wherein the processor uses one or more ratios of light transmission between duplicated sources to correct measurements of the target analyte concentration.

22. The apparatus of claim 21, wherein the processor uses multivariate analysis to estimate the effect of spatial distances between each of the plurality of light sources in the light generation module; and
  remove any resulting errors in measurement of the target analyte.

23. The apparatus of claim 22, wherein the multivariate analysis is at least one of: (1) principal component analysis; (2) multiple regression; (3) factor analysis; and (4) partial least square analysis.

24. The apparatus of claim 23, wherein:
  the plurality of light bands includes at least two sets of light bands such that a first difference between the sums of the received intensities of said sets of light bands in the narrow beam which has passed through or reflected from the sample is a function of the concentration of the target analyte in the sample and is independent of the concentrations of the alternate analytes in the sample;
  the measurement module further comprises means to determine a second difference between averages of said sums of the received intensities of the sets of light bands; and
  the processor uses data from the measurement module for determining the concentration of the target analyte in the sample using said second difference between the averages of sums of the received intensities of the sets of light bands.

25. The apparatus of claim 24, wherein the sample is at least one of: (1) a living organism; (2) a material of biologic origin; and (3) an agricultural product.

26. The apparatus of claim 25, wherein the target analyte is glucose and wherein the sample is a part of a human body.

27. A method of measuring a concentration of a target analyte in a sample containing at least one alternate analyte, the method comprising:
  generating a plurality of independently controlled light wavelength bands;
  switching a plurality of light bands between two or more predetermined waveband intensity distributions;
  combining the plurality of light bands into a narrow light beam;
  directing the narrow light beam onto the sample;
  detecting the light beam having passed through or reflected from the sample;

measuring the intensity of the light beam which has passed through or reflected from the sample;

determining the concentration of the target analyte based on a measured net difference in the intensity between two waveband intensity distributions in the measured light beam which has passed through or reflected from the sample, wherein the switched predetermined waveband intensity distributions are chosen to make said measured net difference in intensity sensitive to the concentration of the target analyte and insensitive to the concentration of at least one alternate analyte; and correcting the analyte concentration measurement using light transmission data from one or more light sources which have been duplicated at different locations in space.

28. The method of claim 27, wherein generating a plurality of independently controlled light wavelength bands further comprises:

monitoring the internal temperature of at least one of the plurality of light sources using at least one of: (1) a thermocouple; (2) a thermistor; and (3) a voltage drop measurement apparatus adapted to measure voltage drop across a semiconductor junction of the at least one of the plurality of light sources; and calibrating output of the plurality of light sources according to their internal temperatures.

29. A method of measuring a concentration of a target analyte in a sample containing at least one alternate analyte, the method comprising:

generating a plurality of light wavelength bands;
combining the plurality of light bands into a narrow beam;
directing the narrow beam onto the sample;
detecting the narrow beam having passed through or reflected from the sample;
measuring an intensity of the narrow beam which has passed through or reflected from the sample;
determining the concentration of the target analyte based on the measured intensity of the narrow beam which has passed through or reflected from the sample;
wherein generating a plurality of light bands further comprises generating a plurality of light bands using a plurality of light sources, each of the plurality of light sources generating one or more of the plurality of light bands;
wherein one or more of the plurality of light sources generating a single light band are duplicated at different spatial locations within the light generation module; and
wherein determining the concentration of the target analyte further comprises using one or more ratios of light transmission between duplicated sources to correct measurements of the target analyte concentration.

30. The method of claim 29, wherein determining the concentration of the target analyte further comprises:

using multivariate analysis to estimate the effect of spatial distances between each of the plurality of light sources in the light generation module; and removing any resulting errors in measurement of the target analyte.

31. The method of claim 30, wherein the multivariate analysis is at least one of: (1) principal component analysis; (2) multiple regression; (3) factor analysis; and (4) partial least square analysis.

32. The method of claim 31, wherein:

generating the plurality of light bands further comprises generating at least two sets of light bands such that a difference between the measured intensities of combined said sets of light bands in the narrow beam having passed through or reflected from the sample is a function of the concentration of the target analyte in the sample and is independent of the concentrations of the alternate analytes in the sample, measuring the intensity of the narrow beam further comprises measuring an average of the said difference in the measured intensities of the combined sets of light bands; and determining the concentration of the target analyte further comprises determining the concentration of the target analyte in the sample using said average of the difference in the measured intensities of said combined sets of light bands.

33. The method of claim 32, wherein the target analyte is glucose and wherein the sample is part of a human body.

34. The method of claim 29, wherein determining the concentration of the target analyte further comprises determining a generated intensity of each of the said generated plurality of light bands using mathematical techniques from the theory of orthogonal vectors so that a difference between a first measured intensity of a first combined set of light bands in the narrow beam and a second measured intensity of a second combined set of light bands in the narrow beam which have passed through or reflected from the sample is proportional to the concentration of the target analyte and insensitive to the concentration of at least one alternate analyte.

35. The method of claim 34, wherein determining the concentration of the target analyte further comprises choosing said generated intensity of each of the plurality of generated light bands to maximize the amplitude of said difference between the measured intensities of a first and a second combined set of light bands in the narrow beam using a linear programming technique.

36. An apparatus for measuring a concentration of a target analyte in a sample containing at least one alternate analyte, the apparatus comprising:

a light generation module comprising light sources for generating a plurality of light wavelength bands each band of a narrow wavelength;

the light generation module switching each of the plurality of light wavelength bands between two or more predetermined intensities;

a light combination module comprising a plurality of light-directing optical elements for combining the plurality of light bands into a narrow beam;

a detector module for receiving light having passed through or reflected from the sample;

a measurement module for measuring a sum of the intensities of the plurality of light bands which have passed through or reflected from the sample; and a memory module for retaining settings of the predetermined intensities of each of the plurality of light bands emitted by the light generation module, wherein said settings are chosen so that the sum of the intensities of the light which has passed through or reflected from the sample is a function of the concentration of the target analyte.

37. An apparatus for measuring a concentration of a target analyte in a sample containing at least one alternate analyte, the apparatus comprising:

alight generation module comprising light sources and a first at least one circuit for generating a plurality of light wavelength bands each band of a narrow wavelength;

the light generation module switching each of the plurality of light wavelength bands between two or more predetermined intensities;

a light combination module comprising a plurality of light-directing optical elements for combining the plurality of light bands into a narrow beam;

a detector for receiving light having passed through or reflected from the sample;

a measurement module comprising a second at least one circuit for measuring a sum of intensities of the plurality of light bands which have passed through or reflected from the sample; and a memory module for retaining settings of the predetermined intensities of each of the plurality of light bands emitted by the light generation module, wherein said settings are chosen so that the sum of the intensities of the light which has passed through or reflected from the sample is a function of the concentration of the target analyte.

38. The apparatus as in any one of claims 1, 21, 36 and 37, in which the light generation module switches each of the plurality of light sources between the two predetermined intensities in a synchronous manner such that in each state each of the plurality of light sources are at one of the two predetermined intensities, wherein in at least one state at least two light sources are at non-zero intensity levels.

* * * * *